United States Patent
Kennedy

(10) Patent No.: US 9,918,672 B2
(45) Date of Patent: Mar. 20, 2018

(54) SYSTEMS AND METHODS FOR ASSESSING SWEAT GLAND OUTPUT

(71) Applicant: Daniel L. M. Kennedy, Minneapolis, MN (US)

(72) Inventor: William R. Kennedy, St. Paul, MN (US)

(73) Assignee: Daniel L.M. Kennedy, Minneapolis, MN (US)

( * ) Notice: Subject to any disclaimer, the term of this patent is extended or adjusted under 35 U.S.C. 154(b) by 0 days.

(21) Appl. No.: 15/153,940

(22) Filed: May 13, 2016

(65) Prior Publication Data
US 2016/0249847 A1  Sep. 1, 2016

Related U.S. Application Data

(63) Continuation-in-part of application No. 13/838,480, filed on Mar. 15, 2013, now Pat. No. 9,339,225.

(51) Int. Cl.
*A61B 5/00* (2006.01)
*A61N 1/30* (2006.01)

(52) U.S. Cl.
CPC .......... *A61B 5/4266* (2013.01); *A61B 5/0077* (2013.01); *A61N 1/30* (2013.01)

(58) Field of Classification Search
CPC ......... A61N 1/30; A61N 1/303; A61B 5/4266
See application file for complete search history.

(56) References Cited

U.S. PATENT DOCUMENTS

| 3,753,099 A | 8/1973 | Kleinberg et al. |
| 4,502,044 A | 2/1985 | Farris et al. |
| 8,548,570 B2 * | 10/2013 | Freeman ............. A61B 5/0059 600/407 |

(Continued)

FOREIGN PATENT DOCUMENTS

| WO | WO-2013152087 A2 | 10/2013 |
| WO | WO-2014143733 A1 | 9/2014 |

OTHER PUBLICATIONS

Riedl et al. "Spatial extension of sudomotor axon reflex sweating in human skin." Journal of the Autonomic Nervous System. vol. 69, Issues 2-3, Apr. 30, 1998, pp. 83-88.*

(Continued)

*Primary Examiner* — Meredith Weare
(74) *Attorney, Agent, or Firm* — Schwegman Lundberg & Woessner, P.A.

(57) ABSTRACT

Various methods may apply iodine on a test area of a subject and allow the applied iodine to dry. Sweating may be triggered in the test area. Triggering sweating may include introducing acetylcholine (ACh) using iontophoresis into dermis within an iontophoresis area. An indirect response to introduction of the ACh may be monitored. Monitoring the indirect response may include applying starch tape over the iodine-painted test area to monitor sweat production from individual sweat glands (SGs) outside of the iontophoresis area, wherein sweat production for each functional SG results in a sweat spot on the starch tape, and taking a series of digital images, using a digital camera, of the starch tape when the individual SGs are producing sweat and causing sweat spots on the starch tape. The digital images of sweat spots may be analyzed to analyze sweat production from the individual SGs.

19 Claims, 24 Drawing Sheets

(56) References Cited

U.S. PATENT DOCUMENTS

| | | | |
|---|---|---|---|
| 9,339,225 B2 | 5/2016 | Kennedy | |
| 2004/0136579 A1 | 7/2004 | Gutenev | |
| 2007/0249913 A1* | 10/2007 | Freeman | A61B 5/0059 600/300 |
| 2008/0081964 A1 | 4/2008 | Zakrzewski | |
| 2010/0179403 A1 | 7/2010 | Martinsen et al. | |
| 2011/0152643 A1 | 6/2011 | Xue et al. | |
| 2012/0165626 A1 | 6/2012 | Irina et al. | |
| 2013/0137991 A1 | 5/2013 | Fright et al. | |
| 2013/0245388 A1 | 9/2013 | Rafferty et al. | |
| 2014/0275862 A1 | 9/2014 | Kennedy | |
| 2015/0057515 A1 | 2/2015 | Hagen et al. | |

OTHER PUBLICATIONS

Illigens et al. Sweat testing to evaluate autonomic function. Clin Auton Res. Apr. 2009; 19(2): 79-87, Published online Nov. 6, 2008.*

"U.S. Appl. No. 13/838,480, Final Office Action dated Oct. 23, 2015", 9 pgs.

"U.S. Appl. No. 13/838,480, Non Final Office Action dated Jul. 6, 2015", 17 pgs.

"U.S. Appl. No. 13/838,480, Notice of Allowance dated Jan. 20, 2016", 5 pgs.

"U.S. Appl. No. 13/838,480, Response filed Oct. 6, 2015 to Non Final Office Action dated Jul. 6, 2015", 8 pgs.

"U.S. Appl. No. 13/838,480, Response filed Dec. 22, 2015 to Final Office Action dated Oct. 23, 2015", 6 pgs.

"International Application Serial No. PCT/US2014/027816, International Search Report dated Jul. 11, 2014", 3 pgs.

"International Application Serial No. PCT/US2014/027816, International Preliminary Report on Patentability dated Sep. 24, 2015", 7 pgs.

"International Application Serial No. PCT/US2014/027816, Written Opinion dated Jul. 11, 2014", 5 pgs.

Dulguerov, P., "Parotidectomy complications. New techniques for their objective evaluation, prevention and treatment", Ph.D. Thesis, Faculty of Medicine, University of Geneva, (1999), 7 pgs.

Fealey, R. D., et al., "Thermoregulatory sweating abnormalities in diabetes mellitus", Mayo Clin. Proc., 64(6), (1989), 617-628.

Gagnon, D., et al., "Modified iodine-paper technique for the standardized determination of sweat gland activation", J. Appl. Physiol., 112, (2012), 1419-1425.

Gibbons, C. H., et al., "QDIRT: quantitative direct and indirect test of sudomotor function", Neurology, 70(24), (2010), 2299-2304.

Gibbons, C. H., et al., "Quantification of sudomotor innervation: a comparison of three methods", Muscle Nerve, 42(1), (2010), 112-119.

Kennedy, W. R., "Collateral Reinnervation of Sweat Glands", Ann. Neurol., 15, Sakuta, (1984), 73-78.

Kennedy, W. R., et al., "Rodent Eccrine Sweat Glands: A Case of Multiple Efferent Innervation", Neuroscience, 11(3), (1984), 741-749.

Low, P. A., et al., "Quantitive sudomotor axon reflex test in normal and neuropathic subjects", Ann Neurol., 14(5), (Nov. 1983), 573-80.

Provitera, V., et al., "Evaluation of sudomotor function in diabetes using the dynamic sweat test", Neurology, 74(1), (2010), 50-56.

Randall, W. C., "Quantitation and regional distribution of sweat glands in man", J. Clin. Invest., 25(5), (Sep. 1946), 761-767.

Sato, et al., "Regiona land individual variations in the functionof the human eccrine sweat gland", J Invest Dermatol ; 5 4 (6 ):443-9 ., (Jun. 1970).

* cited by examiner

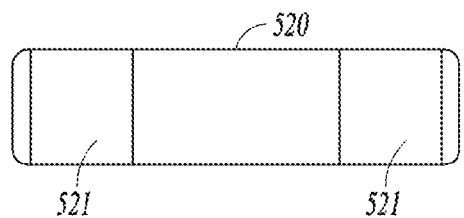
FIG. 5A
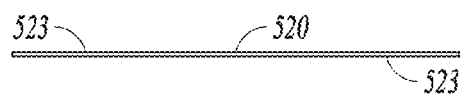
FIG. 5B
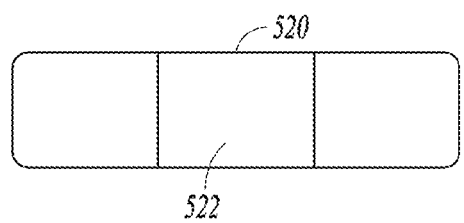
FIG. 5C
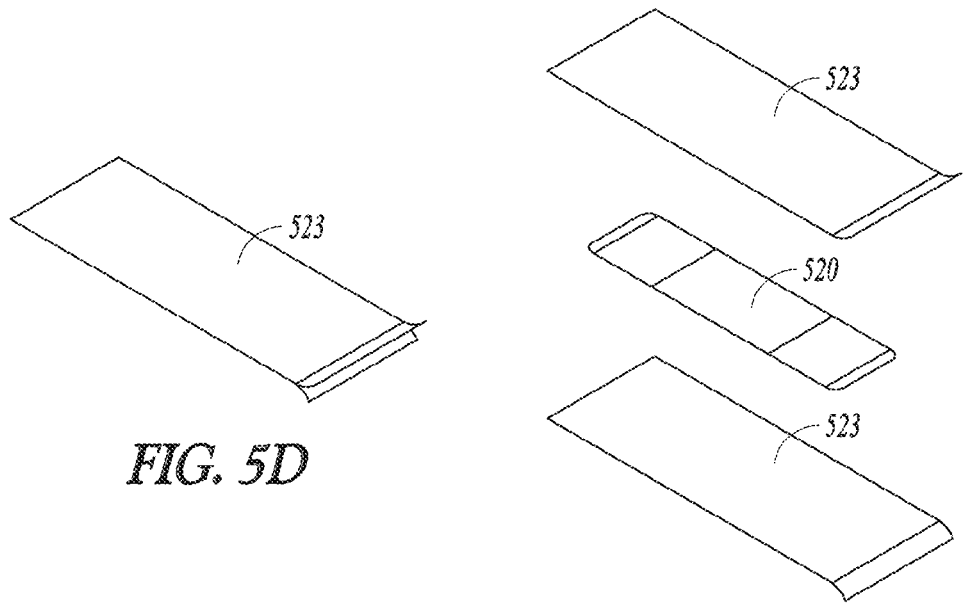
FIG. 5D
FIG. 5E

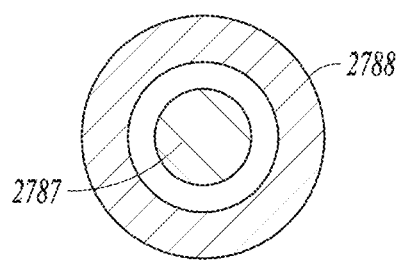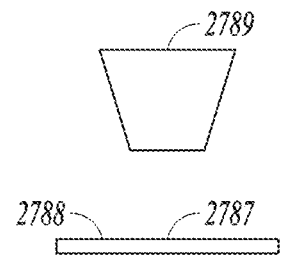
*FIG. 27A*  *FIG. 27B*
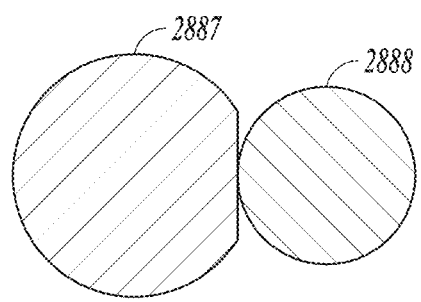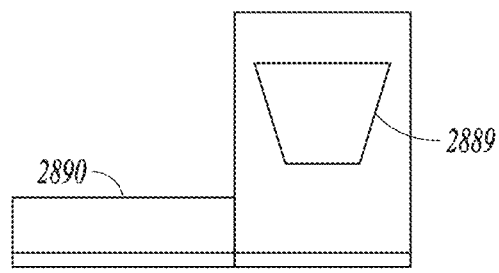
*FIG. 28A*  *FIG. 28B*

SYSTEMS AND METHODS FOR ASSESSING SWEAT GLAND OUTPUT

CROSS REFERENCE TO RELATED APPLICATIONS

This application is a continuation-in-part application of U.S. patent application Ser. No. 13/838,480, filed on Mar. 15, 2013, entitled "SYSTEMS AND METHODS FOR ASSESSING SWEAT GLAND OUTPUT," which is herein incorporated by reference in its entirety.

STATEMENT OF GOVERNMENT SUPPORT

This invention was made with government support under grant number NIH Grant 1R41NS078965-01 awarded by the National Institutes of Health. The government has certain rights in the invention.

TECHNICAL FIELD

This application relates generally to medical testing systems, devices and methods and, more particularly, to systems, devices and methods for assessing output from sweat glands (SGs).

BACKGROUND

Neuropathy is a diseased condition of the nervous system. There are many types of neuropathy. Some examples of neuropathy include, but are not limited to, diabetic neuropathy, chemotherapy-induced peripheral neuropathy (CIPN) human immunodeficiency virus (HIV), and alcoholic neuropathy.

SGs are activated by sudomotor nerves. Neuropathy often affects these sudomotor nerves. One way of analyzing a neuropathic condition of a patient is to evaluate the patient's ability to sweat. The following sweat tests for diagnosing neuropathy are known.

The quantitative sudomotor axon reflex test (QSART) is the most common test. It tests the volume of water produced by SGs in a 1-2 sq. cm area of skin (sweat water/area). Testing begins by iontophoresis of acetylcholine (ACh) into a ring of skin to stimulate SGs in the ring to sweat maximally. The sudomotor nerves (axons) innervating the SGs are also excited. These axons propagate the excitatory impulses proximally that reach the spinal level. However, excitation also flows peripherally at axon branch points toward the skin and excites SGs in other areas of the skin including an area in the center circle of the device (this is the reflex). Air is passed over this center circle to pick up the water that is measured over time. Water is produced only during iontophoresis due to the short survival of acetylcholine in the body. The QSART is mainly used in research studies, and is discussed in the following paper: Low P A, Caskey P E, Tuck R R, Fealey R D, Dyck P J. Quantitative sudomotor axon reflex test in normal and neuropathic subjects. Annals of Neurology. 1983; 14:573-580.

Another sweat test is the silastic mold test. This test was described in the Kennedy lab. The silastic mold test stimulates maximal sweating by iontophoresis of pilocarpine, and measures the number of activated SGs and their approximate secretion volume. The sweating skin is wiped dry and the area is then quickly covered with silastic material. Sweat secreted from SGs pushes into and leaves an impression in the still soft silastic material before the silastic material completely dries. The silastic material drying time may be about 4 minutes. The dried silastic mold can be viewed through a microscope at low magnification by shining light through the mold. The thinned areas that were indented by the sweat drops look like holes. These holes are easily counted. The diameter of the holes may be measured to calculate approximate volume. Thus, the silastic mold test may be used to provide a count of all active SGs in the area of skin tested and the approximate size of sweat droplets. The number of active SGs decreases as neuropathy progresses. The silastic mold test is discussed in the following paper: Kennedy W R, Sakuta M, Quick D C. Rodent eccrine sweat glands: a case of multiple efferent innervation. Neuroscience [0306-4522] Kennedy, W R yr: 1984 vol: 11 iss: 3 pg: 741-749.

Another sweat test is the thermoregulatory test, which shows body areas that do not sweat when the body is heated, presumably because the nerves to the SGs in those areas have degenerated. The anterior body of the patient is dusted with an indicator powder containing alizarin red that turns from orange to purple when wet with sweat water. SGs in non-darkened skin are presumed to be unable to produce water because of nerve degeneration. The thermoregulatory test may be used to determine whether the patient is suffering from neuropathy and if so, where the neuropathy is located. The thermoregulatory test is discussed in the following paper: Fealey R D, Low P A, Thomas J E. Thermoregulatory sweating abnormalities in diabetes mellitus. *Mayo Clin Proc.* 1989 June; 64(6):617-28.

Another sweat test is the quantitative direct and indirect axon reflex testing (QDIRT) which evaluates sudomotor nerve function by measuring both the direct and axon-reflex mediated sweat response. SGs are stimulated by acetylcholine iontophoresis. A mixture of alizarin red, corn starch and sodium carbonate is quickly applied and digital photographs are taken $1/15$ sec. for 7 min. It is difficult to avoid some evaporation. Sweat droplets are quantified by number, size and percent area over the area of interest, separating between direct and indirect sweat production. QDIRT is discussed in the following paper: Gibbons C H, Illigens B M, Centi J, Freeman R. QDIRT: quantitative direct and indirect test of sudomotor function. Neurology. 2008 Jun. 10; 70(24):2299-304. doi: 10.1212/01.wnl.0000314646.49565.c0. PMID: 18541883 [PubMed].

Another sweat test is the Dynamic Sweat Test (DST) developed by the Nolano lab in Italy and the Kennedy lab in Minnesota. The DST test may coat a sticky side of transparent tape with starch on the sticky side, and then place the tape onto the skin. The tape forces the sweat to spread laterally in a thin spot instead of a droplet. The edges of the dark spot are sharply imaged. The areas of the spots are measured at two times. The first time is just after tape is applied to the skin and the second time is when adjacent spots become confluent. If calibrated to known amounts of water, these two measurements can be used to manually calculate a change of a mean spot size over time (proportional to rate), mean sweat volume per $cm^2$ skin and volume per skin area stimulated. The DST has minimal to no evaporation of the sweat, and also provides maximal stimulation over 40 minutes by using pilocarpine to stimulate the sweat. DST is discussed in the following paper: Provitera V, Nolano M, Caporaso G, Stancanelli A, Santoro L, Kennedy W R. *Evaluation of sudomotor function in diabetes using the dynamic sweat test.* Neurology. 2010 Jan. 5; 74(1):50-6. doi: 10.1212/WNL.0b013e3181c7da4b. PMID: 20038772

It is desirable to increase the accuracy of evaluating the peripheral nervous system in order to make an earlier diagnosis of peripheral neuropathy and to more sensitively evaluate the progression or improvement of the neuropathy.

For example, it may be desirable to quantitatively show if a drug is helping or injuring individual patients at an early stage.

SUMMARY

Disclosed herein are systems, devices and methods for assessing output from sweat glands (SGs). Various embodiments measure features of sweating from a single SG to provide an objective and highly sensitive measure of sudomotor nerves that activate SGs. This measure of sudomotor nerves may be used to evaluate patients with neuropathy, including diabetic neuropathy, chemotherapy-induced peripheral neuropathy (CIPN) human immunodeficiency virus (HIV), alcoholic neuropathy and numerous other types of neuropathy.

Various method embodiments may apply iodine on a test area of a subject and allow the applied iodine to dry. Sweating may be triggered in the test area of the subject. Triggering sweating may include introducing acetylcholine (ACh) using iontophoresis into dermis, wherein the ACh is introduced into the dermis within an iontophoresis area. An indirect response to introduction of the ACh may be monitored. Monitoring the indirect response may include applying starch tape over the iodine-painted test area to monitor sweat production from individual sweat glands (SGs) outside of the iontophoresis area, wherein sweat production for each functional SG results in a sweat spot on the starch tape, and taking a series of digital images, using a digital camera, of the starch tape when the individual SGs are producing sweat and causing sweat spots on the starch tape. The digital images of sweat spots may be analyzed to analyze sweat production from the individual SGs.

Various system embodiments may include a sweat test device configured to be applied to a test area on a test subject. The test area on the test subject may include dried iodine. The sweat test device may be configured to detect sweat production of individual sweat glands (SGs) within the test area. The sweat test device may include an iontophoresis component to deliver acetylcholine (ACh) through iontophoresis to an iontophoresis area and an imaging component physically connected to the iontophoresis component. The imaging component may include a digital camera and a starch tape placed over an opening to the digital camera. The imaging component may be configured such that the digital camera is capable of focusing the on the starch tape when the starch tape is placed over the opening to the digital camera. The imaging component is configured to take a series of digital images of the starch tape while starch tape is pressed against an indirect monitoring region of the test region, which is outside of the iontophoresis area.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

FIGS. 5A-5C illustrate planar and side views of an embodiment of starch test strip, FIG. 5D illustrates a perspective view of the completed package, and FIG. 5E illustrate an exploded view of the packaged test strip.

FIGS. 27A-B illustrate an example in which both a direct response and an indirect response may be monitored.

FIGS. 28A-B illustrate another example in which both a direct response and an indirect response may be monitored.

DETAILED DESCRIPTION

Figure 1:
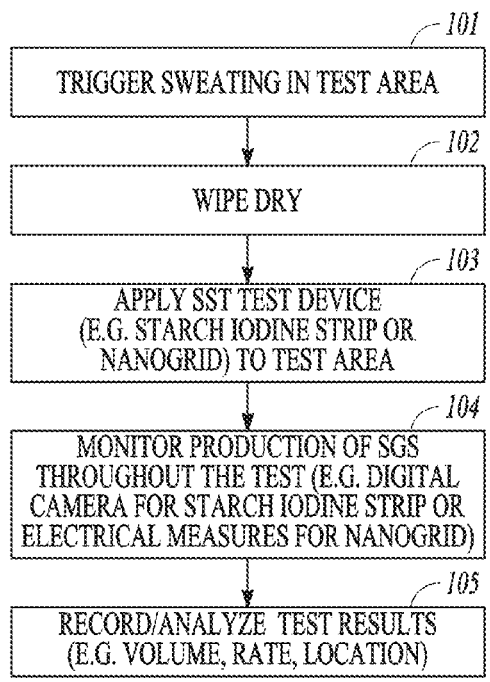
FIG. 1 illustrates an example of an SST flow diagram that may be used to evaluate peripheral neuropathy using a sweat test.

The following detailed description of the present subject matter refers to the accompanying drawings which show, by way of illustration, specific aspects and examples or embodiments in which the present subject matter may be practiced. These are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The diagnosis of neuropathy is usually made by detecting loss in one or more types of nerve activity, such as touch, pain, vibration, sweating or muscle function, or made by detecting abnormal nerve structure (pathology). If less sensitive tests are used, the neuropathy may progress and cause more nerve damage before detection. This delay in detection is undesirable because, as the damage to each nerve increases or as more nerves are damaged, it is less probable that the neuropathy can be halted or that the nerves can recover.

For example, cancer chemotherapy and diabetes are common causes of neuropathy in the USA. Both cause peripheral numbness, pain, decreased sweating, abnormal circulation, and eventually weakness. If diagnosed early, both are potentially treatable. In chemotherapy-induced neuropathy, chemicals used to treat cancer may not be tolerated by the patient. The patient may experience numbness and severe pain which are frequent complications of chemotherapy. A therapist has a better opportunity to adjust dosages, substitute agents or add a protective agent to moderate or stop neuropathy if it can be determined earlier that the patient has low tolerance of the drugs used. Unfortunately, the minimal changes in function that first signal impending neuropathy escape detection by existing tests. Rather, existing tests detect changes in function after significant nerve degeneration has occurred. In elderly persons diabetic neuropathy usually develops before glucose levels reach the level accepted to diagnose diabetes. An early diagnosis of neuropathy can alert a patient and physician, allowing the patient an opportunity to address the condition through diet, exercise and other preventive measures to prevent diabetes and worsening of neuropathy.

The Sensitive Sweat Test (SST) is an objective, quantitative and highly-sensitive test that we use to diagnosis peripheral neuropathy early, when the probability for reversal is greatest. The SST device embodiments are convenient, affordable, and easily used in medical clinics, at the bedside or even in the home. SST is capable of reporting volume/area, but also capable of reporting the more detailed information about individual SG sweat rate and volume and information about active SG number and SG distribution. This sweat data for individual SGs is desirable, as it appears that each SG may have its own characteristic secretion rate. Furthermore, SGs recruit in a defined order, much like motor units. Dysfunction of secretion features, recruitment or features of sweat flow (smooth or pulsatile) at the level of the single SG are early indicators of beginning neuropathy, and early detection of neuropathy provides better options for treating the neuropathy.

The SST, as disclosed herein, addresses limitations of the QSART, silastic mold test, thermoregulatory test, QDIRT and DST. The SST provides a more quantitative, sensitive and accurate test required for early diagnosis and detection of the progress of neuropathies. The SST is also easier to perform. In contrast, existing methods only recognize progression after gross changes of function over a prolonged time period cause patient symptoms. For example, QSART provides a sweat volume/area result, but does not provide data on sweat rate, individual SG rate, individual SG volume, SG number, or SG distribution. Furthermore, the instrument for performing the QSART is expensive.

Although the silastic mold test provides a count of all active SGs in the area of skin tested and the approximate size of sweat droplets, there are many artifacts that resemble droplets and increase SG counts. Additionally, the total and individual SG volume is significantly underestimated because much of the sweat is secreted after the mold has hardened. Thus, these later secretions do not leave an impression in the mold and therefore are not recorded. Further, the silastic mold test does not provide dynamic data on SG rate.

The thermoregulatory test does not quantify sweat volume, SG number or SG distribution. Rather, the thermoregulatory test only shows the gross distribution of where sweating is not present.

Some limitations of QDIRT are that acetylcholine (unlike pilocarpine) is rapidly destroyed in the body. As such, the full stimulation of SGs is short lived. Thus, some SGs may stop secreting sweat even before the imaging to obtain results begins. As such, the number of SGs is underestimated. For example, the estimated number of SGs using QDIRT may be half the number of SGs using the silastic method. Additionally, QDIRT has problems with estimating volume, because sweat evaporates with the exposure to air and this evaporation lowers estimated volume. Also, camera images of 3-D sweat droplets have indistinct margins because the starch is merely sprinkled onto the sweating skin. As a result, the estimated volumes of 3D sweat droplets can be inaccurate. QDIRT does not quantify the rate of secretion, volume of secretion per SG or SG size accurately.

The DST also has limitations. For example, manual measurements were used to obtain sweat spot diameter at two times: after the tape is applied, and after adjacent spots become confluent. As the DST relies on these two manual measurements to obtain sweat spot diameter, the calculations are limited to mean rate and mean volume. The DST test cannot obtain individual SG rate or volume. Further, DST relies on commercial camcorder imaging at a distance, which is unsatisfactory for the required precision of the measurements to provide individual SG rate or volume. The distribution pattern is analyzed by visual inspection only.

FIG. 1 illustrates an example of a flow diagram that may be used to evaluate peripheral neuropathy using the SST sweat test. At 101, significant sweating at a test area on the skin of the patient is triggered or induced. The induced sweat at the test area is wiped dry at 102, and an SST device is quickly applied to the test area 103 for use in monitoring the productions of the SGs throughout the test 104. As the SST is a sensitive test capable of analyzing the sweat production of each SG, test results such as, but not limited to, the sweat volume, rate and location of each SG may be recorded and analyzed 105. One embodiment of the SST uses starch tape and camera images to analyze the sweat production, and another embodiment of the SST uses a nano grid of nanoconductors to analyze the sweat production. These embodiments are described in detail below. The applied SST device 103 may be the starch tape, which also may be referred to as a starch iodine strip as a combination of starch and iodine are used by the digital camera to monitor sweat production 104. The applied SST device 103 may be a nano grid of nanoconductors that can be monitored at 104 to detect or measure electrical changes caused by sweat production.

Figure 2:
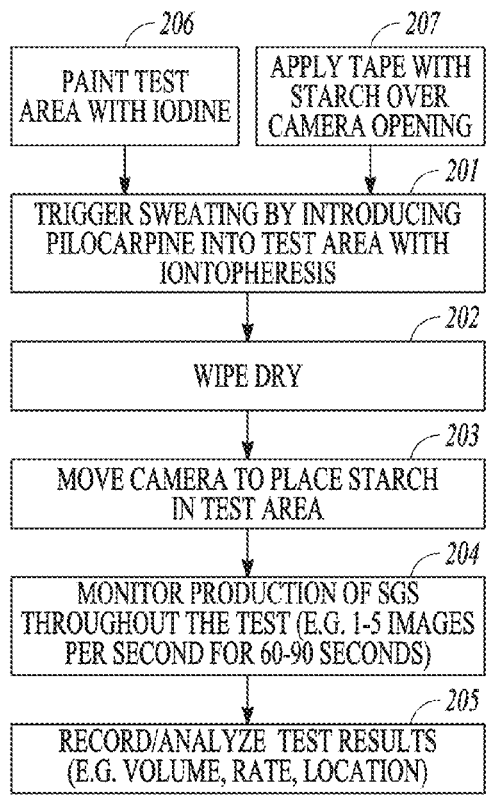
FIG. 2 illustrates an example of a starch tape embodiment that may be used to evaluate peripheral neuropathy during a sweat test.

FIG. 2 illustrates an example of a starch tape embodiment that may be used to evaluate peripheral neuropathy during a sweat test. As illustrated in the figure, preparations for making the sweat test measurements include painting the skin of the patient in the test area with iodine 206 and also include applying a transparent tape with starch on the tape over a camera opening 207. For example, a short strip of transparent tape, such as high quality packing tape, may be coated with a thin layer of starch such as corn starch. This tape will be attached over an opening of a small camera at a distance that allows the camera to focus on the starch. An iodine solution applied to the skin may be a 1% iodine solution. The iodine solution allows the starch to turn dark when in contact with sweat water. The dark spots produced at sweat duct openings provide good contrast and promote the precise imaging required to monitor and analyze the sweat production of each SG in the test area.

At 201, significant sweating at a test area on the skin of the patient is triggered or induced by introducing pilocarpine into the test area with iontophoresis. Pilocarpine may be used to stimulate SGs in the dermis of the skin to cause maximal sweating. For example, the SGs may be stimulated to secrete sweat by introducing 1% pilocarpine into the skin dermis within an approximately 2 $cm^2$ area using iontophoresis. The 2 $cm^2$ area contains approximately 200 sweat pores, depending on skin location. Iontophoresis uses electric current to deliver the pilocarpine into the skin. A simple stimulator may be used to apply the iontophoresis. For example, an approximately 2 milliamp direct current may be delivered to the area for approximately 5 minutes. More sophisticated stimulators may be used, such as a dual stimulator that simultaneously stimulates more than one skin area, measures time of current flow and has safety features that prevent excessive current. A small free standing, battery-powered unit may be designed for greater convenience and motility. The patch between the anode stimulator pad holder and skin may contain a buffer, $KNO_3$ or $KSO_4$, and pilocarpine. The ionophoresis may shift the pH and undesirably reduce the ability of the pilocarpine to be introduced in to the skin. The buffer reduces the problems with pH changes. The cathode pad may contain only $KNO_3$ or $KSO_4$ in solution or be in a gel.

After a short interval (often 10 minutes) after iontophoresis to assure the desired SG secretion, the iodine painted skin is quickly wiped dry with a swift motion 202 and the camera is immediately pressed against the skin 203. As sweat water begins to exit from each of the sweat pores within the tested area, the sweat water contacts the starch/iodine and forms a tiny dark spot that begins to expand due to the force of continuous sweating. Pressure by the tape prevents formation of a sweat drop. Instead, sweat is forced to flow centrifugally, moving radially away from the sweat pore, between the tape and the skin to form a thin enlarging dark spot. Images of these dark spots may be used to analyze the sweat production. The camera takes a series of images over a period of time to monitor the sweat produced by the SG. For example, the images may be periodically taken one or more times per second, and may continue until adjacent spots coalesce. By way of example, and not limitation, the number of images taken may range from 1-5 images per second for a duration of 60 to 90 seconds. The image rate may be higher to provide more information about incremental changes in the image of the spot for recognition and calculation of sweat flow characteristics, or may be less to provide less information about incremental changes. The results of this test may be recorded and analyzed, as generally illustrated at 205. The imaging of these expanding black spots may be performed by a special short focal length miniature camera and wide angle lens. The camera may have a custom housing that contains field illuminating LEDs, signaling LEDs to indicate computer connectivity and ON/OFF imaging, molded diffusers.

Figure 3:
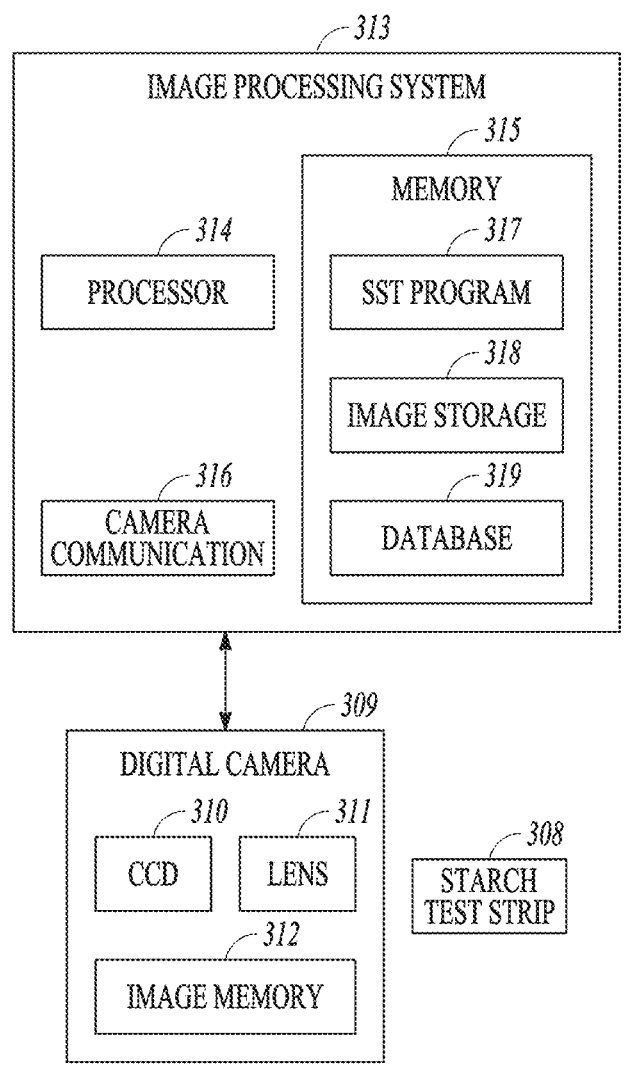
FIG. 3 illustrates an example of an SST system embodiment that images starch on a starch tape to perform a sweat test.

FIG. 3 illustrates an example of an SST system embodiment that images starch on a starch tape to perform a sweat test. The illustrated system includes a starch test strip 308 (also referred to herein as tape). The test strip may be made from a transparent material, on which the starch may be applied. The system also includes a digital camera 309 used to focus on the test strip to detect the dark spots on the starch caused by the sweat water. The camera 309 includes, among other things, an imager 310, such as a CCD (charge coupled device) imager, a lens for focusing the image on the imager, and an image memory for storing images that are taken during the test. CCD sensors are capable of producing high-quality, low-noise images.

An image processing system 313, such as a programmed computer, may be used to communicate with the camera and download the pictures off of the camera. The image processing system 313 may also be used to control the timing of the images taken by the camera. The illustrated system 313 includes a processor 314, memory 315, and camera communication module 316 for communicating with the camera. The functions provided by the system 313 may be provided by hardware, software, and firmware. The memory 315 may be used to store a SST program or programs 317 used to perform the test and analyze the test results, an image storage 318 in which the images from the camera may be loaded, and a database 319 in which test results may be stored.

The system 313 may use the images to calculate the rate of spot expansion and the expanding spot area. The imaged spot area is a virtual two-dimensional image. The rate of spot expansion determined from the two-dimensional images is converted to a sweat rate (volume over time) for each individual SG. For example, the sweat rate may use the units, nanoliters/minute. The expanding area determined from the two-dimensional images is converted to a sweat volume for each individual SG. For example, the sweat volume may be given in nanoliters.

The system 313 may also be configured to determine SG density (SG number/area) and distribution of secreting SGs. Denervated SGs do not secrete. They leave detectable voids in the pattern. Data may be transferred to a database for final calculations and conversions as predetermined by appropriate camera calibrations. The process may be performed one or more times, and the results compared for SG number, distribution and other results as a safeguard of data collection and to assure that pilocarpine stimulation was consistently strong, indicating that the test was applied correctly.

The SST may report SG number and distribution, sweat rate and volume for each of over 200 SGs, plus total rate and volume per skin area. The SST information reflects functional events that occur at the single gland level. Each SG has its individual rate and volume. Additionally, the number and distribution of the SGs that are secreting sweat water, the recruitment and sweat flow characteristics also may be determined.

Figure 4A:
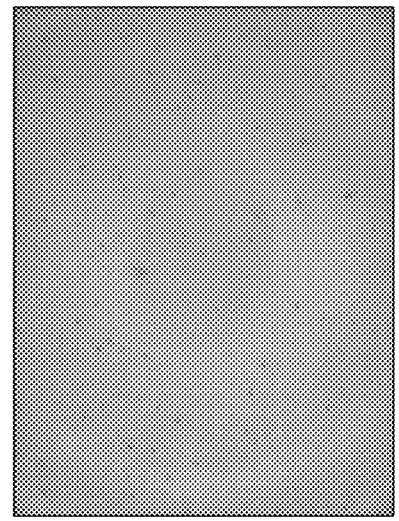
FIGS. 4A, 4B, and 4C illustrate images taken early in the sweat test, in the middle of the sweat test, and late in the sweat test.
Figure 4B:
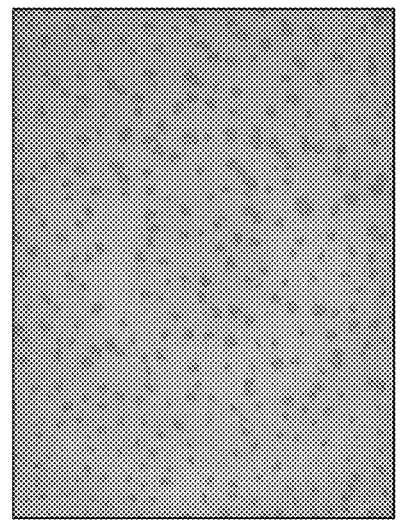
Figure 4C:
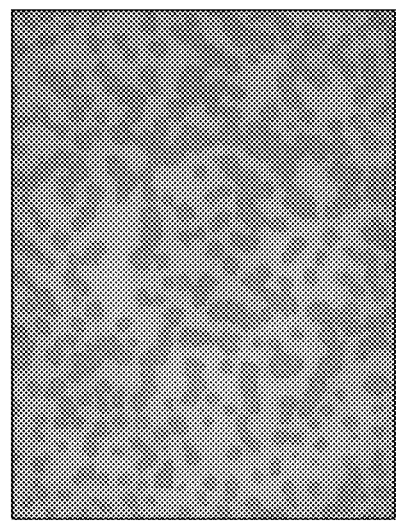

As identified above, SST uses starch-coated transparent tape placed on iodine-coated skin. The tape forces the sweat droplets to flow centrifugally in a flat, expanding spot. As the sweat is limited to expansion in virtually two dimensions and is generally prevented from expanding in a third dimension, the thickness of the expanding spot is generally constant and the spot area is proportional to the sweat volume from the same underlying SG. Each of the enlarging sweat spots may be identified and imaged many times during the test. Spots may be counted and sweat rate and sweat volume may be calculated for each SG. FIGS. 4A, 4B, and 4C illustrate images taken early in the sweat test, in the middle of the sweat test, and late in the sweat test. It can be seen that there are very few dark spots early (FIG. 4A), but that the dark spots appear and grow (FIG. 4B) then merge with adjacent dark spots (FIG. 4C).

FIGS. 5A-5C illustrate planar and side views of an embodiment of starch test strip, FIG. 5D illustrates a perspective view of the completed package, and FIG. 5E illustrate an exploded view of the packaged test strip. One side of the test strip 520 includes two adhesive regions 521 positioned to be used to attach the test strip over the opening of the camera and to position the starch 522, centrally applied on the other side of the test strip, in line with the camera opening. Protective liners 523 may be attached to the test strip to protect the test strip before use. The test strip may be completely transparent, or the test strip may be transparent only where the starch is applied. There are a number of ways to create these strips. One way of placing starch on the strip is to run a web of tape through a trough of starch, and the remove the excess. For example, the web of tape may be unwound from an unwind roll to a first idler roll at a first end of the trough, and then to a second idler roll at a second end of the trough, and then out of the trough and up toward a rewind roll. Excess starch may be removed from tape using a vacuum, using a blower, by scraping, or a combination of methods. Other process may be implemented to deposit a desired amount at a desired location on the tape.

The system is designed to provide a high resolution image for use to accurately detect these dark spots. The starch tape is attached at a fixed distance from the camera lens. In some embodiments, the camera uses a wide angle lens with a short focus length. For example, the SUNEX DSL944 lens may be used. This lens is a multi-element glass lens that provides high resolution up to 8M CCD/CMOS imagers with a format size of 1/2.5 inch. The lens has an overall length from lens front physical surface to the image plane (the starch tape) of 11.3 mm, and an f-stop of F/2.8 with a long depth of focus.

Figure 6A:
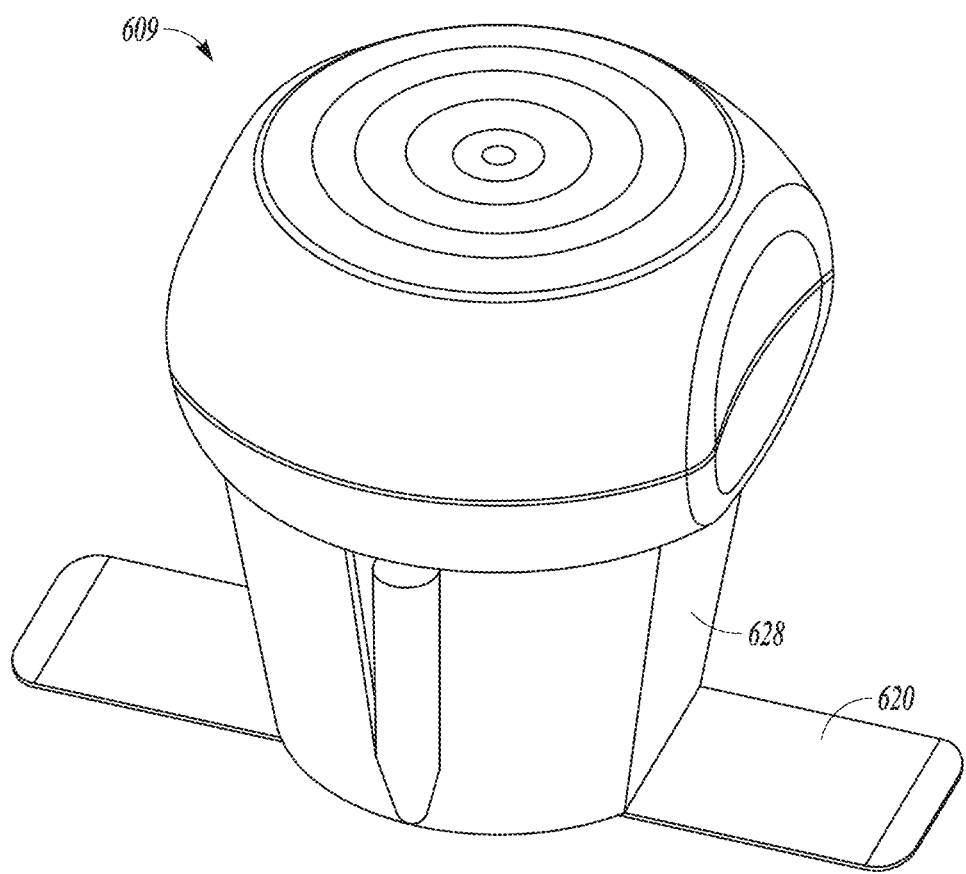
FIGS. 6A-6B illustrate perspective views of the camera with a starch tape placed over a camera opening.
Figure 6B:
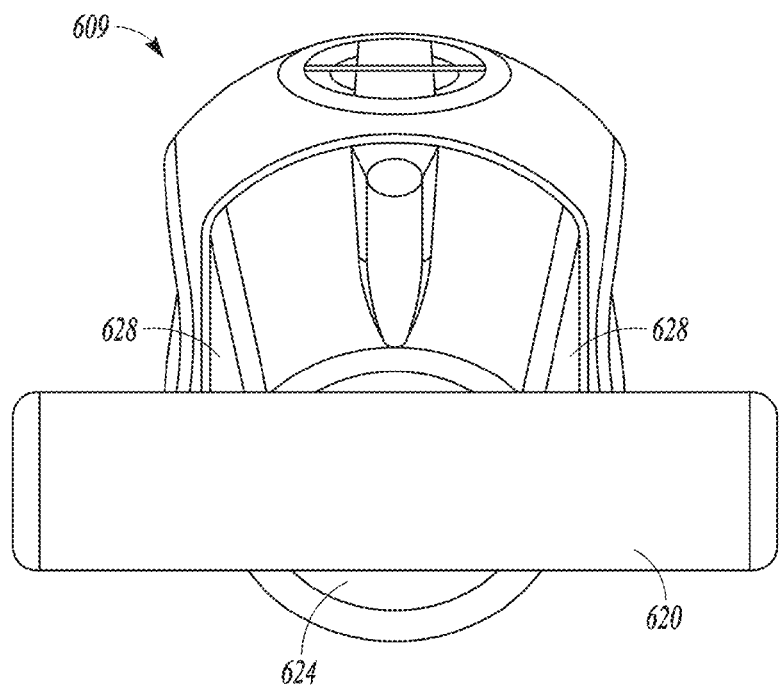
Figure 6C:
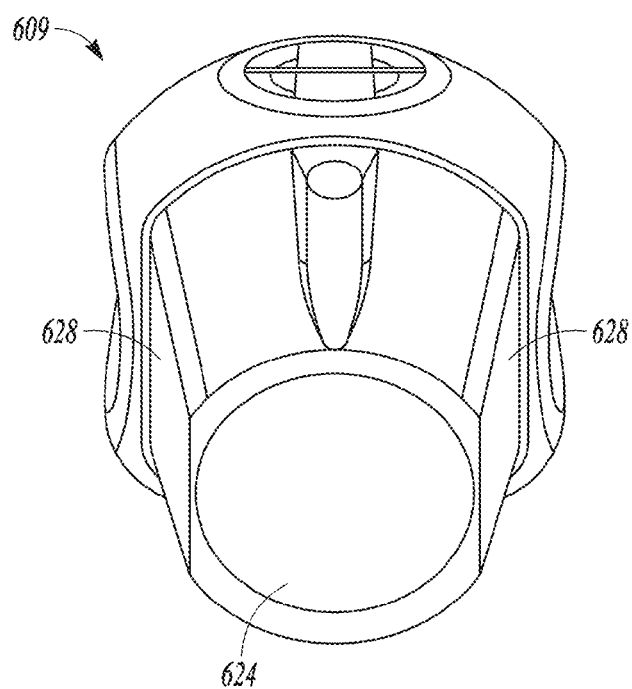
FIG. 6C illustrate the view of FIG. 6B without the starch tape to show a transparent window.
Figure 6D:
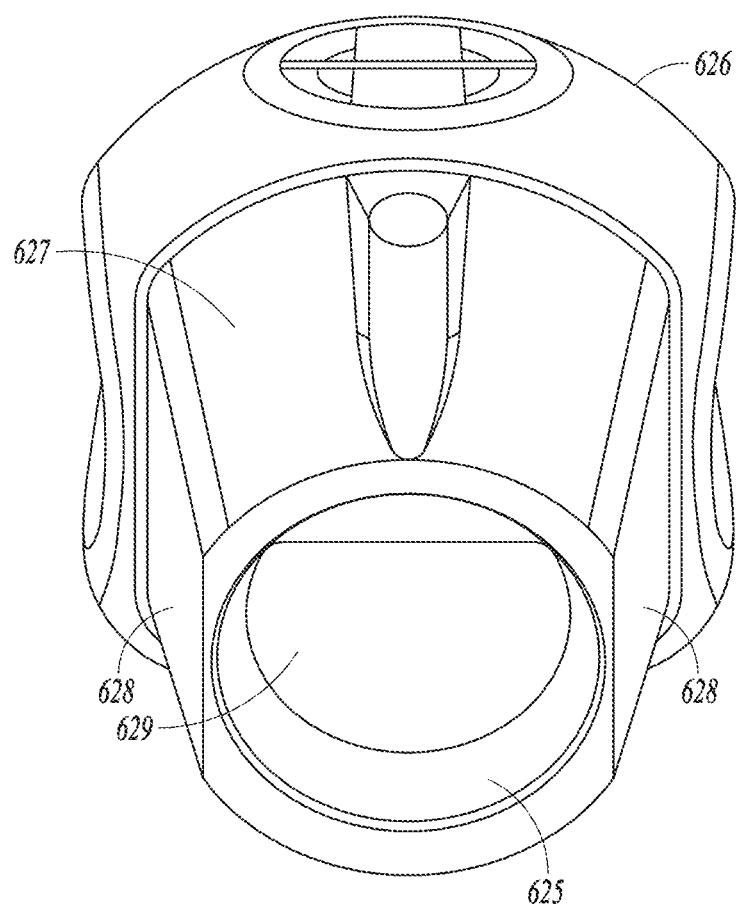
FIG. 6D illustrates the view of FIG. 6D without a transparent window and thus shows the camera opening.

FIGS. 6A-6B illustrate perspective views of the camera 609 with a starch tape 620 placed over a camera opening; FIG. 6C illustrate the view of FIG. 6B without the starch tape to show a transparent window 624, and FIG. 6D illustrates the view of FIG. 6D without a transparent window 624 and thus shows the camera opening 625. The housing of the camera 609 includes a cap 626 which houses the camera component and lens. The cap 626 also has a shape to function as a handle for a user to place the camera against the test subject. The housing of the camera 609 also includes a nose portion 627 which has the camera opening 625 on the end of the nose portion 627. The nose portion may also include other components such as a diffuser 629. The nose portion 627 may be screwed or otherwise fastened to the cap 626. The nose portion 627 may have flat surfaces 628, against which the adhesive portions of the test strip 620 may be pressed. Thus, the test strip 620 may be placed over the camera opening, and the ends of the test strip 620 may be folded back onto these flat surfaces 628. The camera structure is designed so that the image plane of the lens is at the end of the nose portion where the tape is attached.

Figure 7:
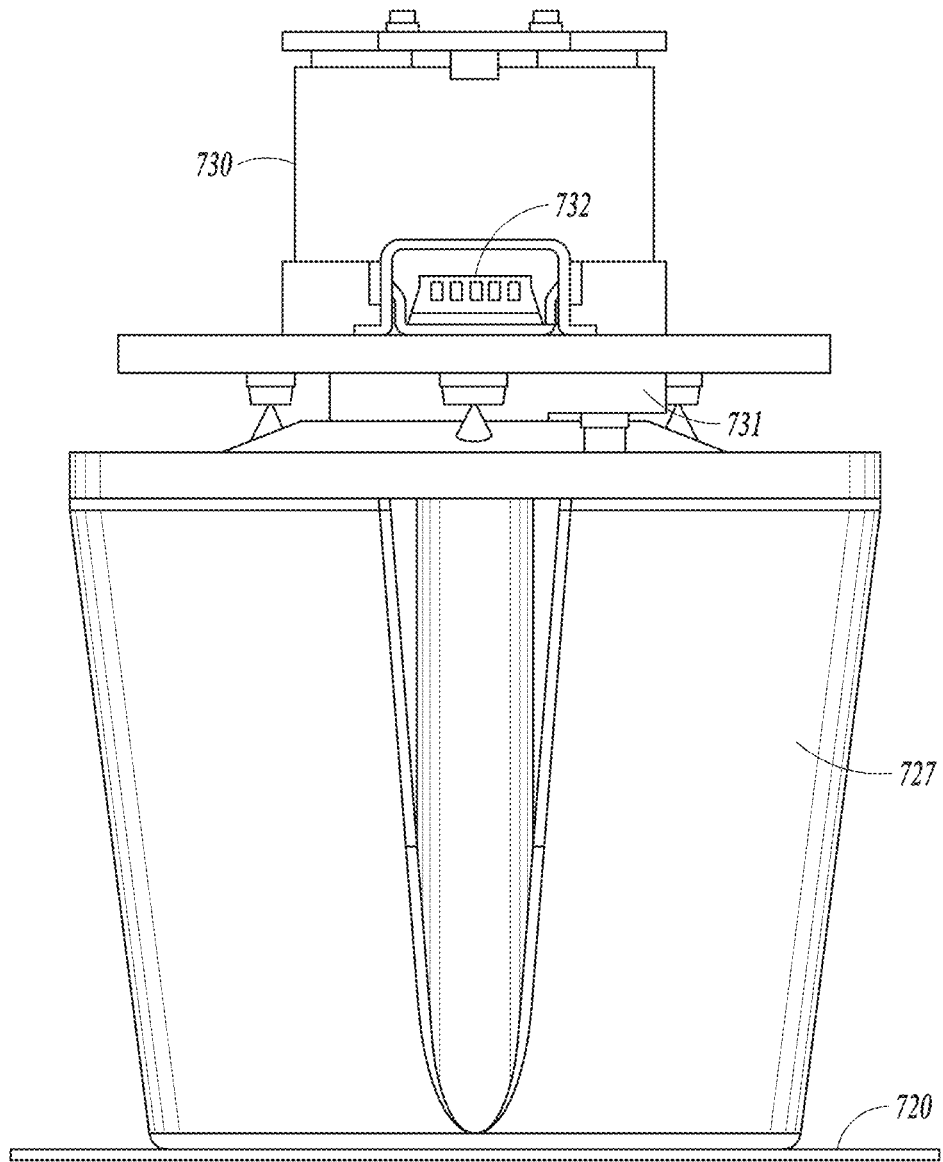
FIG. 7 illustrates a side view of the camera, without the cap, exposing the camera component, which includes the digital imager, and the lens.
Figure 8:
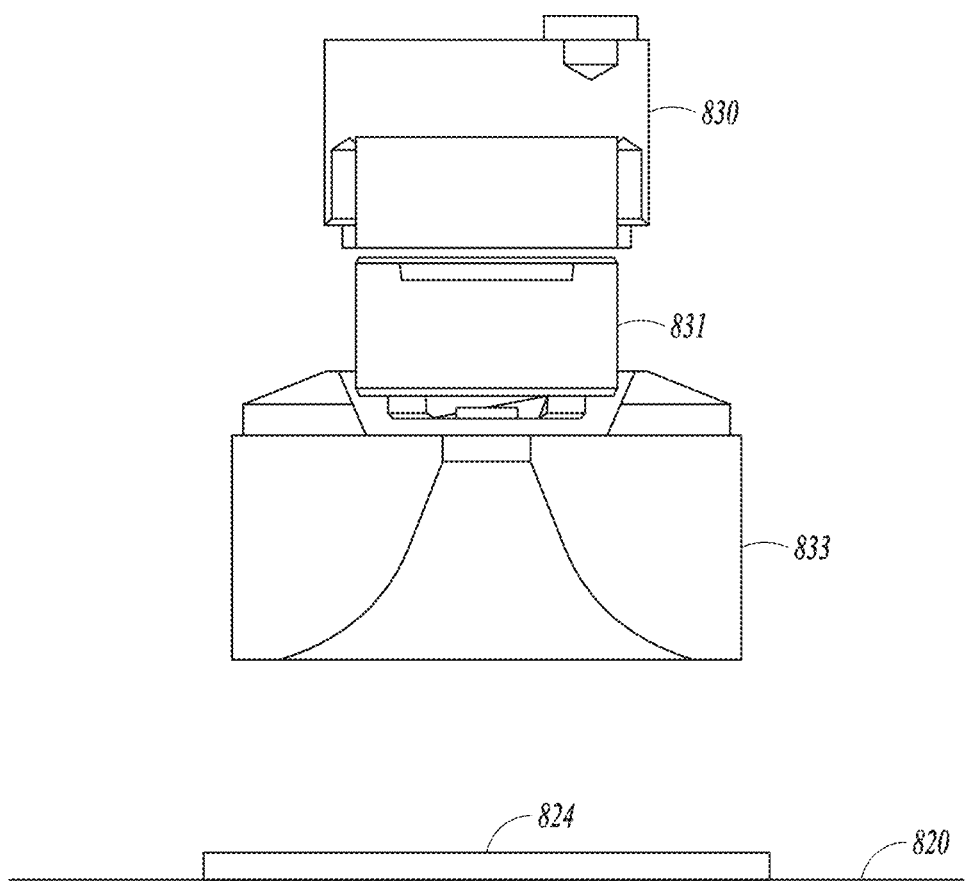
FIG. 8 generally illustrates the fixed distance between the camera lens and the test strip (image plane).

FIG. 7 illustrates a side view of the camera, without the cap, exposing the camera component 730, which includes the digital imager, and the lens 731. The illustration also shows a communication port 732 to receive a communication cable for use to communicate between a computer and the camera. However, the communication is not limited to cable connections, as wireless communication is also possible. The nose portion 727 allows a test strip 720 to be quickly placed on the image plane of the lens 731, and still obtain a high resolution, focused image. FIG. 8 generally illustrates the fixed distance between the camera lens 831 and the test strip 820 (image plane). The figure also illustrates the camera component 830, the diffuser 833, and the transparent window 824 at the end of the nose portion.

Figure 9:
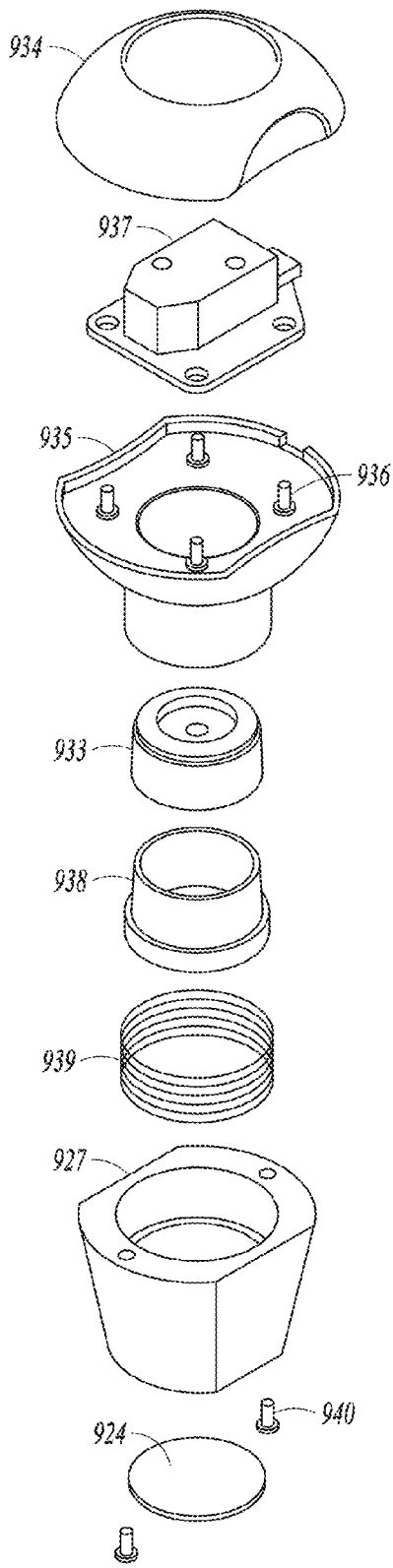
FIG. 9 illustrates an exploded view of an example of the digital camera.

FIG. 9 illustrates an exploded view of an example of the digital camera. The cap of the housing may be formed by a top housing component 934 and a bottom housing component 935, which may be attached together using screws 936. Together, the top and bottom housing components 934 and 935 form a cap that houses the camera circuit card assembly 937. This view also illustrates the diffuser 933, sleeve 938, spring 939, nose portion 927, transparent window 924 and shoulder bolts 940 used to connect the nose portion 927 to the bottom housing component 935. The spring 939 presses against the sleeve 938 and the nose portion 927, which along with the use of the shoulder bolts 940 allow some give when the nose portion 927 is pressed against the test area of the test subject.

Figure 10:
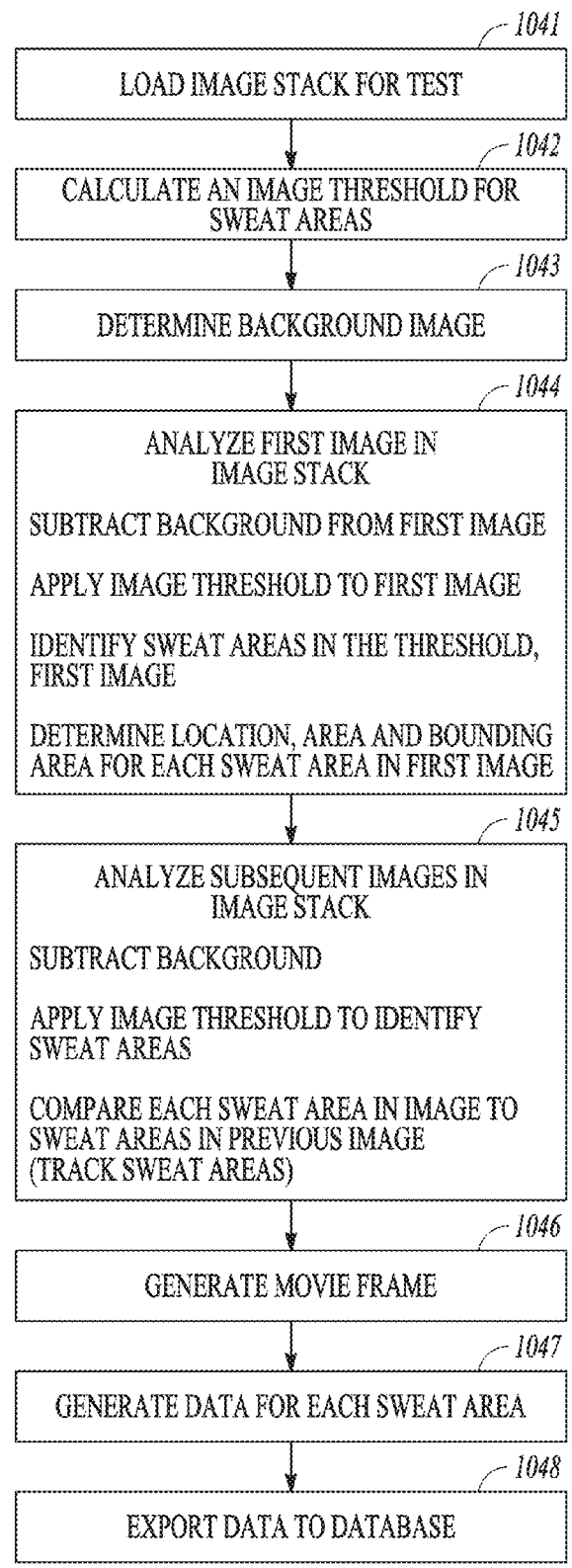
FIG. 10 illustrates a flow diagram of a process for analyzing the images taken during the course of the test.

FIG. 10 illustrates a flow diagram of a process for analyzing the images taken during the course of the test. For example, a series of 1 to 5 images may be taken every second for a duration of about 60 to 90 seconds. In an example, these images are initially stored in the camera, and then loaded into the image processing system for analysis.

At 1041, the image stack is loaded from the camera memory into the memory of the image processing system. At 1042, the image processing system calculates an image threshold for use to determine whether a given pixel represents a sweat area. For example, an image in the middle of the stack is used to generate a threshold. This image is expected to include a number of sweat areas of a relatively large size, but before the sweat areas start to merge with each other. The threshold calculated is dependent on which algorithm is used (SIS, Otsu, Local, or Simple fixed). At 1043, a background image is created from the first image in the image stack. This background image is used to subtract the constant portions of the picture to provide further contrast between the sweat areas and the areas without sweat. The first image has the fewest sweat areas, and thus is expected to mostly represent background. A smoothing process is performed on the first image to create the background image. For example, the first image may be shrunk to ¼ size, a Gaussian blur filter may be applied a number of times (e.g. 5 times) to the shrunken image, and a 3×3 mean filter may be applied to the shrunken image. The 3×3 image uses the average of 9 pixels to determine the value of the pixel in the center of the 3×3 block of pixels. The image may then resized back to original size to be used as the background image. The result is a smooth background.

The first image of the image stack is analyzed at 1044. For example, the background image may be subtracted from the first image, and the resulting first image may then be thresholded using the threshold calculated above. Each pixel in the thresholded image either represents a sweat pixel or a pixel without sweat. This may be envisioned as a black and white image. The thresholded image may then be segmented into sweat areas (spots), and each spot may be identified with a number identifier. For example, the spots in an image may be consecutively numbered scanning the image from left to right and top to bottom. Each spot has an X, Y center location, area, and bounding rectangle. An area of the spot may be calculated from the camera pixel calibration (measured image size/number of pixels), and volume may calculated using a linear fit of area to volume, the slope and intercept that can be determined from an area to volume calibration. Both of these calibrations are further described below.

The subsequent images of the image stack are analyzed at 1045, where the following may be repeated for each analyzed image. The background image may be subtracted from the analyzed image, and the resulting image may then be thresholded using the threshold calculated above. The thresholded image may then be segmented into sweat areas (spots), and each spot may be identified with a number identifier. Each spot is compared to the spots in the previous image so they may be tracked from image to image. If the current spot covers the same pixels as a spot from the previous image, its identifier is changed to that from the previous image. If the current spot has a number that was already assigned in the previous image, but does not overlap a previous spot, its identifier is changed to an unused identifier. If the current spot covers more than one spot from the previous image, its identifier may be changed to the lowest overlapping identifier number from the previous image, or the new spot may be considered merged and its identifier changed to a range of identifiers reserved for merged spots.

At 1046, the images may be combined into a movie frame. The spots may be color-coded by number, with merged spots being colored gray. Once all frames are processed, a list of spots may be generated which includes the spot identifier, start frame, stop frame, start area in mm, stop area in mm, micro liter change, and rate per second. Additional data may be recorded as well, such as data pertaining to intermediate frame(s) between the start and stop frames. This data may be exported to a database.

If the spot area has increased, a value for the area (in pixels for example) may be stored in a table corresponding to its identifier and the frame in concern. If two sweat areas have merged, a new identifier may be assigned and the area is not calculated as it would show a (wrong) sharp jump in the area. The number of uniquely identified spots (sweat areas) may be counted to identify the number of active SGs. Each sweat area, before merging with another sweat area, represents an active SG. The numbers of SGs per $cm^2$ may be derived from this SG count and from a camera calibration that identifies how many pixels fit in a given $cm^2$ area.

Also, a growth rate for each of sweat areas may be calculated. The nomenclature below uses "X" to refer to an earlier sweat area (e.g. from an earlier image frame) and uses "Y" to refer to a later sweat area (e.g. from a later image frame). The X image frame may be the first frame in which the sweat area appeared, and the Y image frame may be the last frame in the test or the last frame before the sweat area merges with an adjacent sweat area. For this X and Y, the rate can be calculated as the average rate for the test. However, the X image frame does not have to be the first image frame and the Y image frame does not have to be the last image frame. For example, as the rate of sweat production in a given SG may vary, it may be desirable to track the sweat rate of each SG throughout the course of the test or for a given portion or portions of the test. A rolling average of "n" images may be used. For example, an average of the sweat area for images 1-5 may be determined for image "3", and average of the sweat area for images 2-6 may be determined for image "4", etc. Larger values of "n" are less responsive to changes in the calculated rate, and smaller values of "n" are more responsive to changes in calculated rate.

Let Ax=area of the sweat area (pixels) at frame x.
Let Ay=area of the sweat area (pixels) at frame y.
n=y−x=Number of frames.

$$\text{Rate of Increase} = (Ay-Ax)/n \text{(pixels/frame)}.$$

The rate of increase maybe converted from pixels per frame to pixels per second using the number of frames that are imaged per second (f).

$$\text{Rate of Increase} = (Ay-Ax)*f/n \text{(pixels/second)}$$

Figure 11:
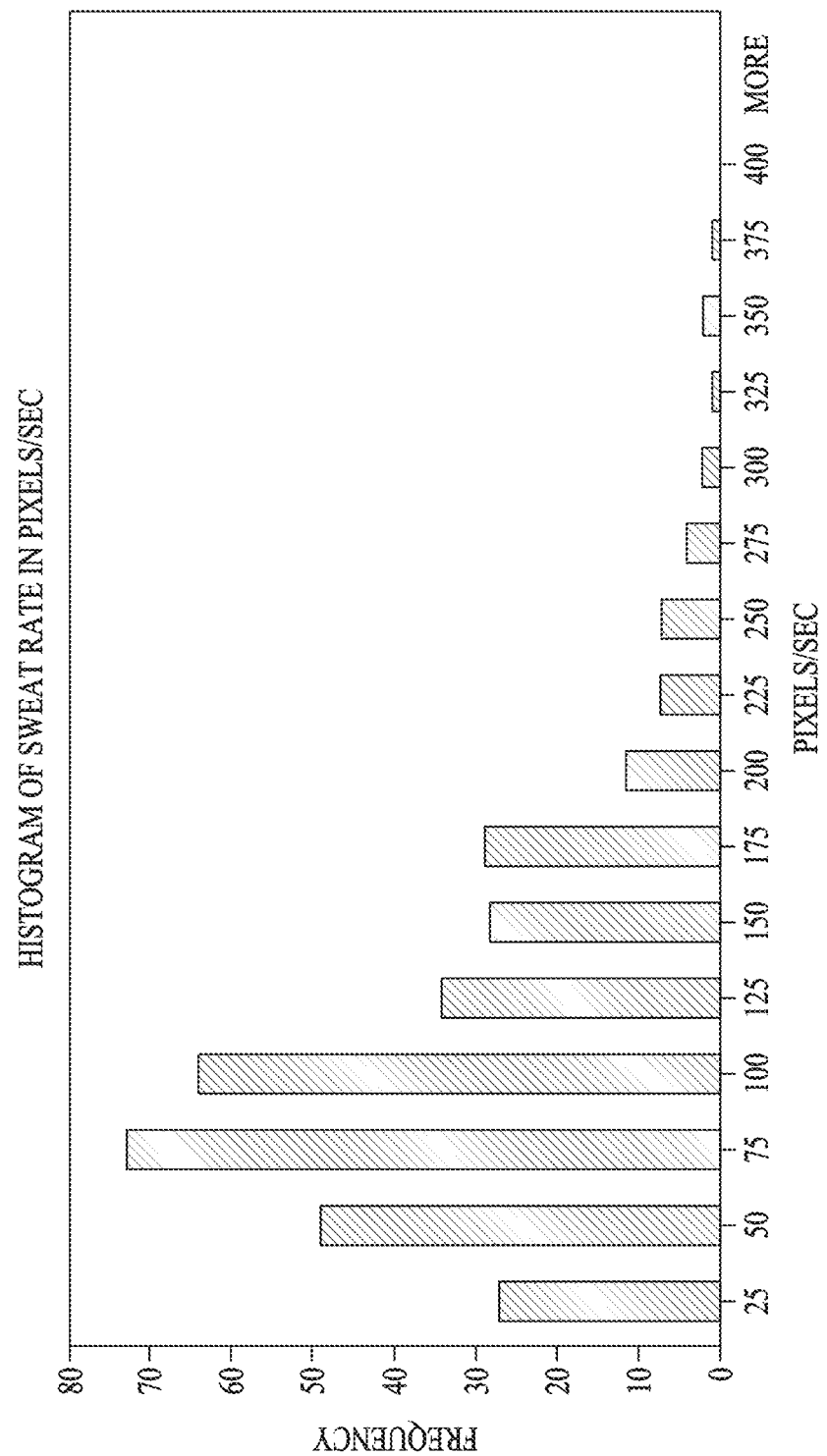
FIG. 11 illustrates a histogram that groups together sweat areas that grow at the same rate, as displayed by the rate of increase in area on the X axis and the number of sweat areas on the Y axis.

The sweat areas that grow at the same rate may be grouped together and plotted in a histogram with the rate of increase in area on the X axis and the number of sweat areas on the Y axis, as generally illustrated as an example in FIG. 11. If a SG does not sweat, a sweat area does not appear on the image frame and there is no record of that SG and that non-active SG is not counted. Correspondingly, the histogram has fewer frequencies overall. So a generally "low" histogram is an indicator of fewer functional SGs in the area imaged.

As the sweat is limited to a space near the skin by the transparent tape, the growth of the sweat area is generally constrained to growth in the generally two-dimensional region along the surface. The thickness of the layer of sweat on the skin is generally constant, and the volume ($ml^3$) of the sweat can be approximated as a linear function of the area ($ml^2$) of the sweat area. An example of a process for converting from an area to volume is provided below.

Each camera device is calibrated to determine the size of the pixels in the images taken by the device, which allows the pixels to be converted into μm. For example, an image may be taken of a micrometer area (e.g. a 4000 μm by 4000 μm area). The image may be opened in rendering software to determine the length of the area in both the X and Y directions (e.g. 608 pixels in both directions). This information maybe used to calculate the size of a pixel in microns (e.g. 4000 μm/608 pixels=6.57895 μm per pixel). That is, one pixel is equal to 6.57895 μm. A second calibration may be performed using a 250 μm by 250 μm area and a similar process may be performed to confirm the ratio between μm and pixels, thus providing a higher level of confidence in the calibrated values.

Figure 12:
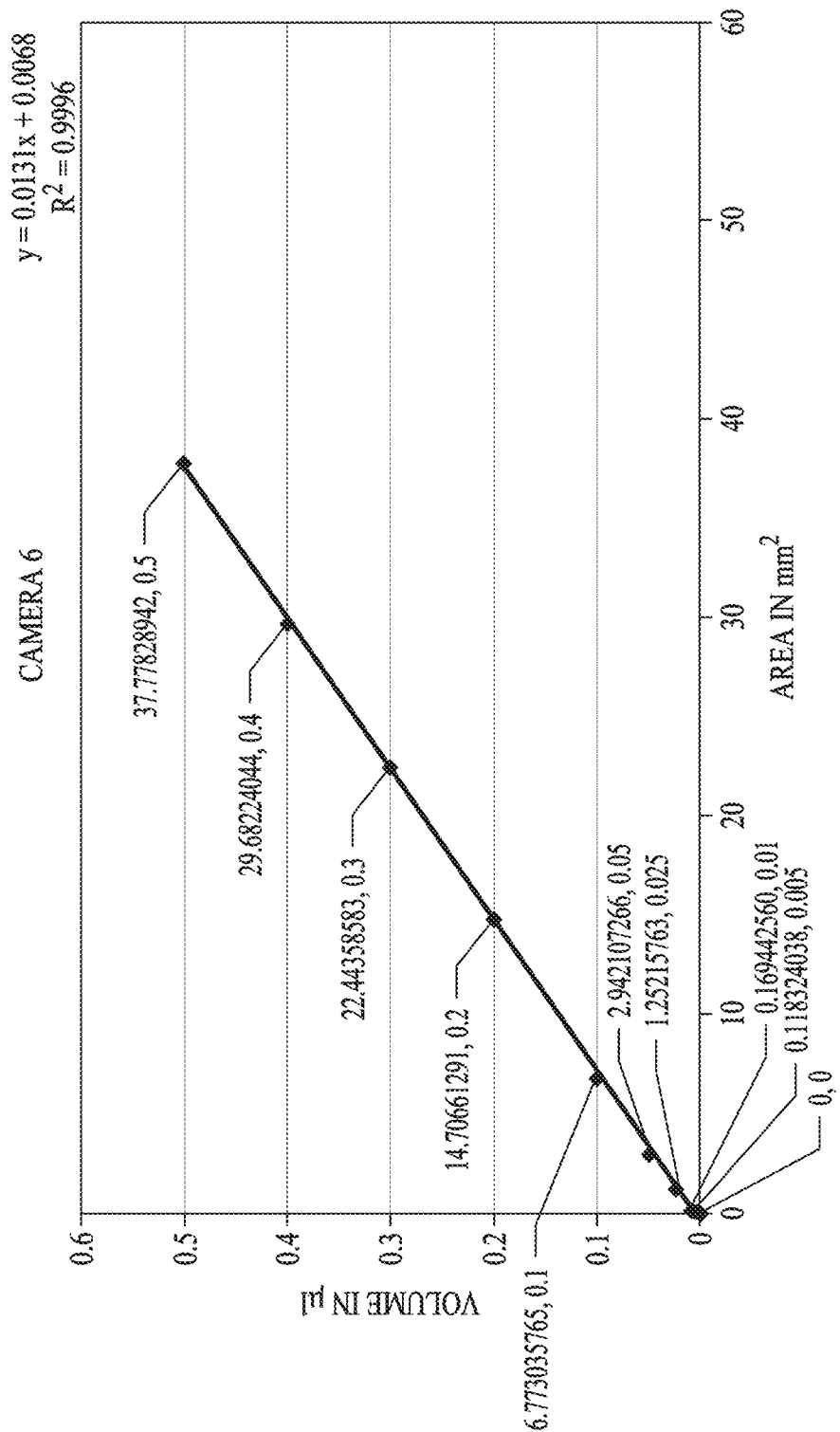
FIG. 12 illustrates a linear equation for converting sweat area to sweat volume derived from a calibration procedure.

The calibration procedure may continue to determine a linear relationship between the sweat area and volume. For example, a very accurate Hamilton pipette may be used to precisely measure volumes of iodine. The measured volumes range from 5 nanoliters (nl) to 500 nl, for example. Each known volume is measured multiple times (e.g. 20), and each one of those is placed on a starch coated tape, then quickly flattened with a clean glass slide and quickly imaged with the camera. The imaged drop may then be opened up in one or more image rendering software programs (e.g. image J and neurolucida). The pixel calibration may be entered (e.g. 6.57895 μm from above) and the area of the volume droplet may be measured in mm². Sampling each volume multiple times (e.g. 20) increases the sample and reduces error in the calibration procedure, as an average of many values may be determined for each volume. Each new camera device should be calibrated. A linear equation (y=ax+b, where Y represents volume and X represents area) may be derived from these plotted points, as generally illustrated FIG. 12. This linear equation functions as a conversion from a measure of area to a measure in volume. The conversion equation may be incorporated into the database along with an identifier of the corresponding camera that was calibrated. Thus, for a given sweat video imported into the database, the camera that was used for imaging may be identified to allow the database to convert the imaged areas into volumes, and to calculate sweat rate (e.g. nl/s). SG density (SGs/cm²) may be determined from a count of sweat droplets within the whole imaged field and from the calibration of the camera.

Some SST embodiments use a nano grid of electrical conductors to test sweating function. This is a nano technology system that is designed to measure SG rate and volume, number of SGs and distribution pattern, which is faster and simpler than imaging the starch-coated transparent tape in the above described system. Furthermore, the nano grid may also be configured to analyze the content of the sweat.

Figure 13:
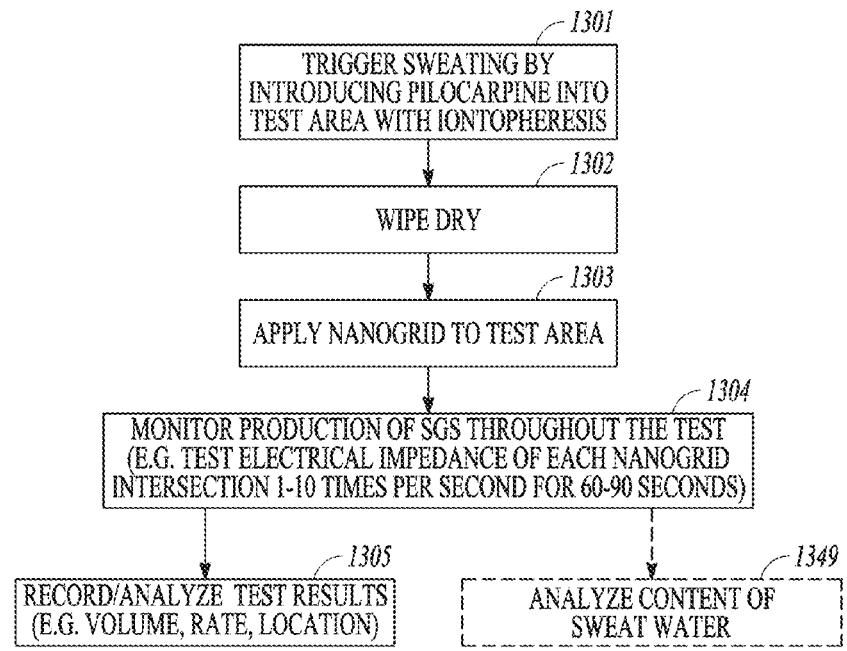
FIG. 13 illustrates an example of a nano grid embodiment that may be used to evaluate peripheral neuropathy to a sweat test.

FIG. 13 illustrates an example of a nano grid embodiment that may be used to evaluate peripheral neuropathy to a sweat test. At 1301, significant sweating at a test area on the skin of the patient is triggered or induced by introducing pilocarpine into the test area with iontophoresis, as was described above. After a short interval (often 10 minutes) after iontophoresis to assure the desired SG secretion, the skin is quickly wiped dry with a swift motion 1302, and the nano grid is immediately applied to the skin 1303. As sweat water begins to exit from each of the sweat pores within the tested area, the sweat water contacts the wires at the intersection, causing a significant drop in resistance. At 1304, the sweat production of the SGs are monitored throughout the test. For example, the electrical impedance of each nano grid intersection may be tested 1 to 10 times per second and may continue testing for 60 to 90 seconds. In some embodiments, the SST test may also analyze the content of the sweat water produced during the test 1349.

Figure 14:
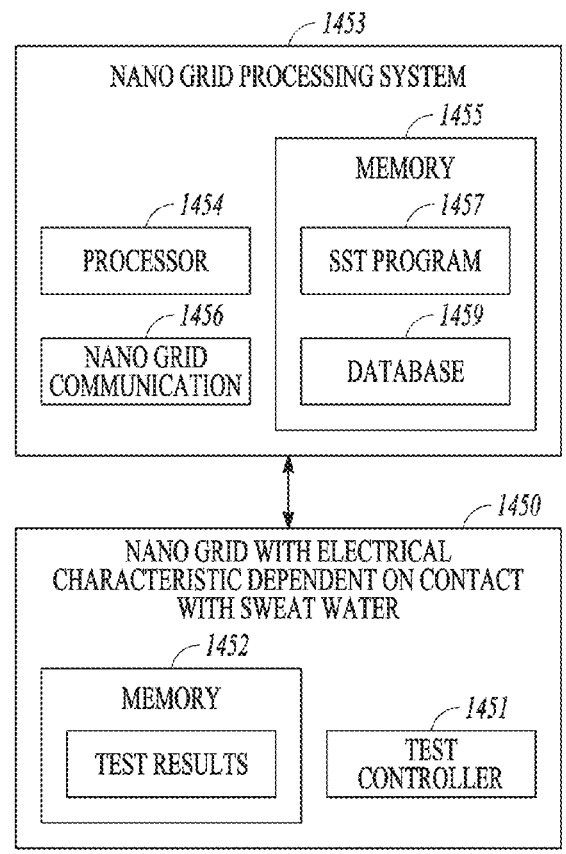
FIG. 14 illustrates an example of an SST system embodiment that uses a nano grid of electrical conductors to perform a sweat test.

FIG. 14 illustrates an example of an SST system embodiment that uses a nano grid of electrical conductors to perform a sweat test. The illustrated system includes a nano grid assembly 1450 that includes the grid of electrical conductors, and that further includes a test controller 1451 configured to test the nano grid and determine which intersections of the nano grid are in contact with the sweat water, based on a detectable electrical change in the wires. The nano grid assembly may also include a memory 1452 for storing test results during the course of a test. In some examples, at least some of these processes may be performed by the nano grid processing system.

The nano grid processing system 1453, such as a programmed computer, may be used to communicate with the nano grid assembly 1450 and download the test results from the memory 1452. The image processing system 313 may also be used to control the timing and procedure for testing the intersections. The illustrated system 1453 includes a processor 1454, memory 1455, and nano grid communication module 1456 for communicating with the nano grid assembly 1450. The functions provided by the system 1453 may be provided by hardware, software, and firmware. The memory 1455 may be used to store a SST program or programs 1457 used to perform the test and analyze the test results, and a database 1459 in which test results may be stored.

The system 1453 may use the test results to calculate the rate of expansion and the area of the sweat areas for various times during the test. Each intersection of the grid is analogous to a pixel of the imaged sweat area for the starch tape system described above. However, rather than showing a dark (or light) pixel for a corresponding wet area of the starch, a significant change in impedance at an evaluated intersection indicates that sweat has reached the intersection and is forming a conductive path between the intersecting conductors. The grid may be adhered to the skin, similar to the starch tape, to limit the growth of the sweat droplets to be in a narrow layer along the skin surface. Thus, an area to volume linear equation may be derived, similar to the approach described above. The pattern of voltage drops at multiple crossings of nanowires in the grid will provide continuous monitoring of the locations of the moving boundaries of nano liter drops. These will be proportional to the sweat rate of the underlying SGs.

Figure 15:
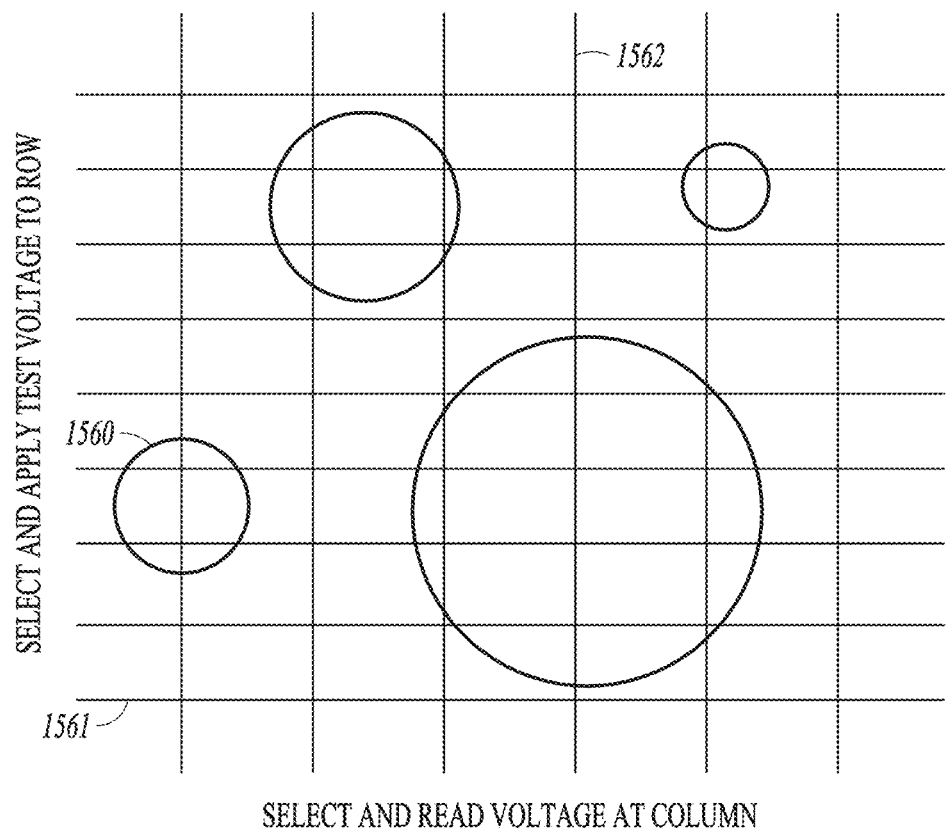
FIG. 15 illustrates sweat water from SGs, and further illustrates intersections in contact with sweat water, and intersections not in contact with sweat water.

FIG. 15 illustrates sweat water 1560 from SGs, and further illustrates intersections 1561 in contact with sweat water, and intersections 1562 not in contact with sweat water. Intersections 1561 have low impedance, and intersections 1562 have high impedance. These data points provided by the intersections are similar to the data points provided by pixel images. By way of example, the intersections may be scanned 1-10, or more, times per second. The scanning method may simply be selecting a row from top to bottom, and for each selected row selecting a column from left to right. Other scanning techniques may be implemented. A standing voltage may be applied to the selected row, and the electrical potential on the selected column may be read to determine whether the intersection is in contact with sweat water. The electrolyte laden sweat water is conductive. Expansion of the continuously secreted sweat water contacts the conductors of the grid. This allows continuous monitoring of the locations of the moving boundaries of nanoliter drops. These will be proportional to the sweat rate of the underlying SGs. Thus, the system may be used to provide similar data as provided by systems that use starch tape. Example of this data include SG density (SG number/area) and distribution of secreting SGs, sweat rate and volume for each of over 200 SGs, plus total rate and volume per skin area.

Figure 16:
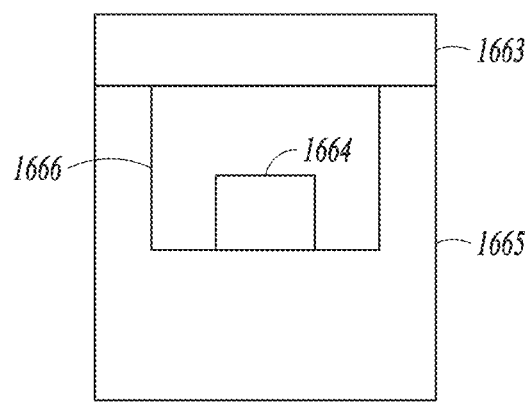
FIG. 16 illustrates an example of a structure of an intersection of the array.

FIG. 16 illustrates an example of a structure of an intersection of the array. Two sets of conductors may be formed to provide a layered structure. In the illustrated example, the conductors within each set run parallel to each other and perpendicular to the conductors in the other set. The illustrated intersection shows a top conductor 1663 that is part of a top set of conductors and a bottom conductor 1664 that is part of a bottom set of conductors. An insulator 1665 generally separates the lines from each other. The insulator may be formed as one or more insulators during fabrication of the nano grid. A pocket 1666 of air is created at every metal line intersection by etching holes through the insulator. Thus, at each intersection, the conductor from one layer is separated from the conductor from the other layer by air, which is an insulator. Thus, the impedance between the two lines is quite large. However, the sweat water is conductive. Thus, when sweat water enters the pocket 1666 and contacts both conductors 1663 and 1664, the impedance between the conductors drops significantly. It is noted that if a standing voltage is applied to one of the conductors, then the conductors are driven with a direct current (DC) and the impedance between the conductors can be referred to as the electrical resistance between the conductors.

The device works by measuring the electrical resistance between the conductors at each intersection, and sweat is detected by a dramatic drop in resistance. The device may exhibit a resistance of about $10^{10}$ to $10^{11}$ ohms between the conductors. When normal saline is applied the resistance drops significantly (e.g. eight orders of magnitude to about 800 ohms). The response time is of order milliseconds.

The device can be rinsed in water and reused indefinitely. Water adsorption due to room humidity or incomplete drying after cleaning will not change the measurement significantly since it is the ions in sweat that actually conduct current.

The ends of the conductors may be connected to multiplexers so that a digital signal can be used to determine the row and column of interest and the resistance can be read back. A single multiplexer may be used to provide control for both the rows and columns of the array. The multiplexor(s) functions as a row select and a column select, to allow electrical connections between a node with a standing voltage and one of the selected conductors and another connection between a sensor and the other of the selected conductors.

Figure 17:
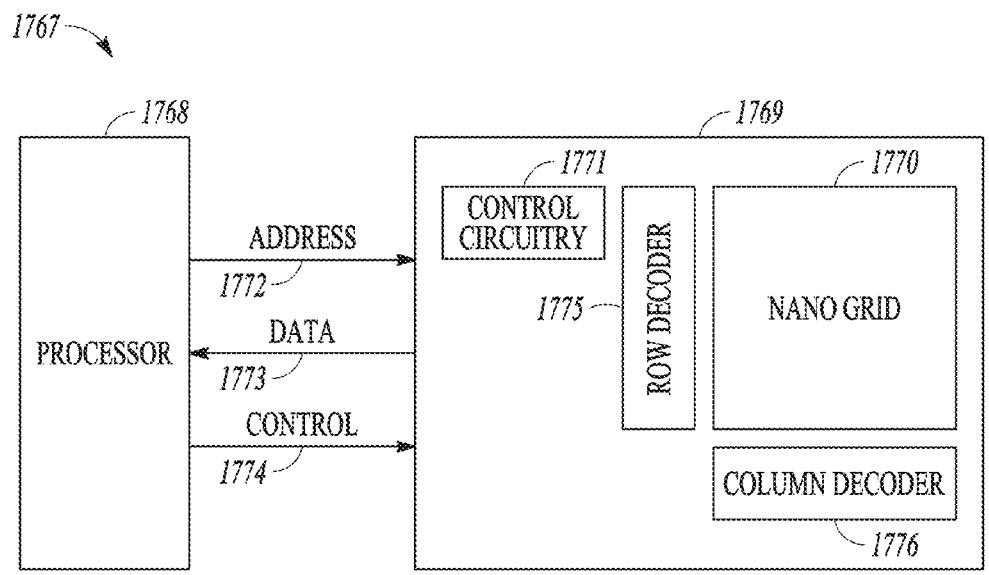
FIG. 17 illustrates an example of a system for reading the electrical resistance of the nano grid intersections.

FIG. 17 illustrates an example of a system for reading the electrical resistance of the nano grid intersections. The system 1767 includes a processor 1768 and a sensor device 1769. The sensor device 1769 includes a nano grid 1770 and control circuitry 1771, and is connected to the processor through an address bus 1772, a data bus 1773 and a control bus 1774. In a read operation initiated by the processor, address information and control information are provided to the sensor device. Row and column decoders 1775 and 1776 use this information to select the row and column to be tested. The resistance determined for the tested intersections may be communicated back to the processor 1768 via the data control bus 1773.

The nano grid may also be configured to identify and quantify the concentrations of the large number of substances in sweat water. These include electrolytes, sugars, peptides, proteins, including antibodies and antibiotics and lipids. Many of the same components are present in blood and extracellular fluid and some in urine. Thus, the nano grid system may be used to quantify SG function to detect peripheral neuropathy early and to analyze electrolytes, peptides and other body constituents routinely sampled in blood and urine. The system takes advantage of the location of SGs on most of the body surface where sweating can be tested non-invasively and inexpensively without patient risk.

As discussed above, sweating provides an early direct measure of nerve abnormalities secondary to chemotherapy induced peripheral neuropathy (CIPN), diabetic, alcoholic and other neuropathies using a simple procedure. Further the content of sweat can also provide important diagnostic clues. Sweat contains electrolytes, peptides/proteins, carbohydrates and other analytes, which may useful with patients suffering from several disorders such as, by way of example and not limitation, diabetes (glucose), cystic fibrosis (chloride), uremia, intoxication or prostatic cancer (prostate stimulating antibody). The device may be used to provide an early detection of exposure to neurotoxins in general.

The nano grid may be integrated with sensors to measure the concentration of selected analytes in the sweat. By way of example and not limitation, chlorine is the marker for the presence of cystic fibrosis. ChemFETs are one example of such a sensor. The ChemFET is similar to a conventional MOSFET, but an organic ion sensitive membrane such as polyurethane, silicone rubber, polyamide, or polystyrene is used in place of the gate electrode. This attachment can be done mechanically or chemically. The choice of membrane and its treatment depend on the target to be sensed.

Figure 18:
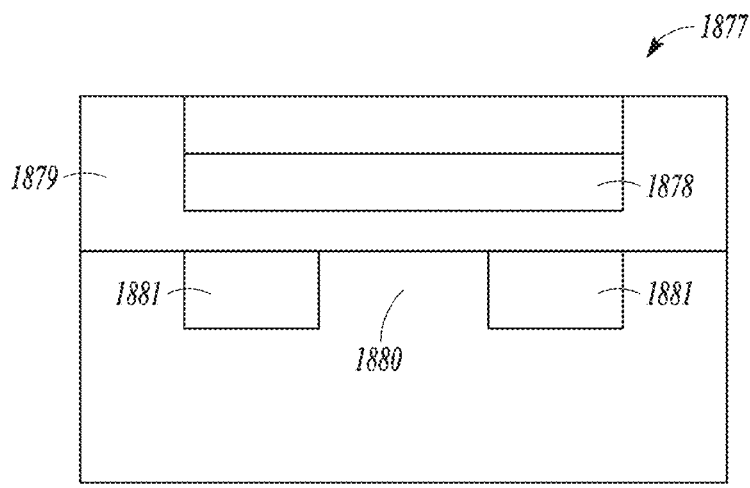
FIG. 18 illustrates a ChemFET.

A MOSFET functions as a switch, as an electrical potential at the gate controls whether current flows between source/drain regions of the MOSFET. The ChemFET operates similarly, except that analyte ions provide the gate control for the FET. FIG. 18 illustrates a ChemFET 1877. When the analyte ions diffuse through the membrane 1878 and reach the surface of the gate insulator 1879, their charge creates an electric field which modulates the carrier density on the surface of the FET and induces a current in the channel 1880 between the source/drain regions 1881 that is easily detected. ChemFETs have been demonstrated that are sensitive to many ionic species including Na+, K+, Ag+, and transition metal cations. Highly specific biological compounds can be incorporated as well for the detection of various organic species. These include glucose oxidase for the detection of glucose, and penicillinase for the detection of penicillin.

The examples provided above describe systems and methods for evaluating SGs in a test area. The size of the test area may be about 2 $cm^2$, which depending on skin location, contains about 200 SGs. Larger areas would test a larger number of SGs and smaller areas would test a smaller number of SGs. Also, the number varies depending upon the location on the body being tested. These examples also illustrate means for evaluating discrete points within the test area to determine whether there is sweat at that point. These discrete points may be referred to as "pixels" whether the discrete points are in a digital image or whether the discrete points are intersections of the nano grid. Each of these discrete points provides a data point for the test area. The distribution of these data points is appropriate to monitor the sweat production of individual SGs within the test area. The number of data points determines the amount of detail ("resolution") for the test.

By way of example and not limitation, a 5 MP camera may be used to image a 2 cm×2 cm region, and the resulting image includes sufficient detail to monitor the sweat production of individual SGs. However, other imaging configurations are possible that still provide the required resolution to monitor the production of individual SGs. Similarly, the nano grid configuration also provides sufficient data points ("intersections") to monitor sweat production of individual SGS. For example, if a 2 cm×2 cm test region is used, one million data points could be obtained by placing 1,000 equally-spaced nanowires in each layer (1,000×1,000=1,000,000). The resolution can be controlled by controlling the number and spacing of the nanowires. The size can be scaled down according to the ability to fabricate the nano grid of nano wires. However, it is not necessary to make the test area square. For example, it may be desirable to fabricate the grid to provide the desired area for testing, but with an aspect ratio between 3:1 to 10:1. For example, 1,000 equally spaced wires in one layer and 5,000 equally spaced wires in the other layer can provide 5 million data points. If the spacing between wires is the same for each layer, the nano grid has a 5:1 aspect ratio.

The above-described system may be used to monitor direct or indirect (axon reflex) responses as will be described below. The system may be used to monitor the effects of peripheral nerve disease on the thin slow conducting unmyelinated sudomotor nerves that control sweating, thus enabling an earlier diagnosis of peripheral neuropathy as well as a more sensitive evaluation of progression or improvement with treatment. These sudomotor nerves conduct at about 1 m/s compared to the much faster 55 to 60 m/s conduction of faster nerves. The inventor currently believes that that the ACh-activated indirect axon reflex method can become a more sensitive indicator of neurogenic abnormalities than the direct response from either ACh or pilocarpine.

Sweating may be induced through iontophoresis of pilocarpine or ACh. As will be discussed in more detail below, both pilocarpine and ACh produce a direct response at the site where the iontophoresis occurred. However, ACh also produces an indirect response (axon reflex response) where sweat glands produce sweat in a different region than where the iontophoresis occurred. The responses for pilocarpine (direct response) and ACh (direct and indirect responses) are illustrated in FIGS. 19 and 20, respectively.

Figure 19:
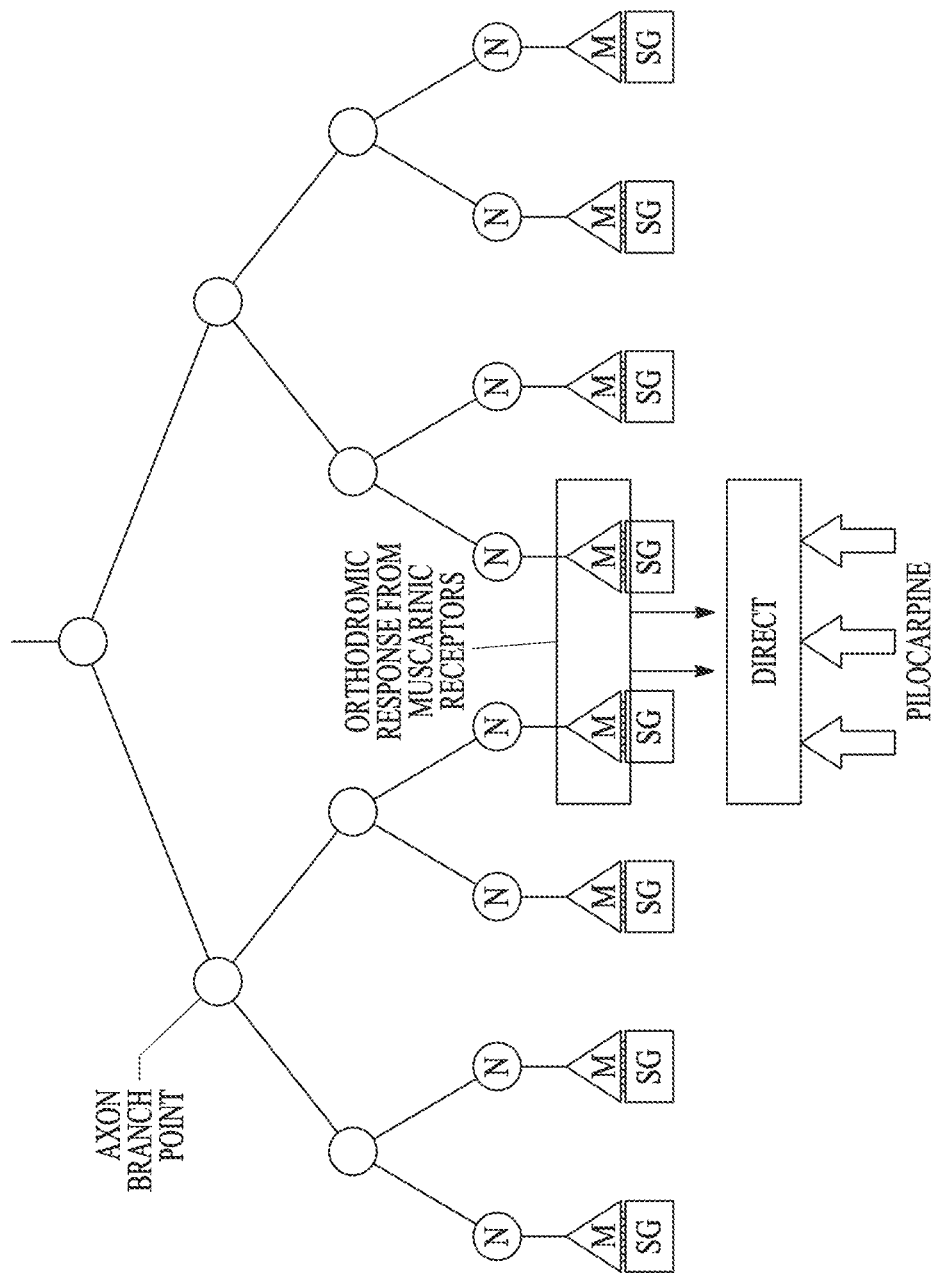
FIG. 19 illustrates a peripheral nerve network and a response to pilocarpine.
Figure 20:
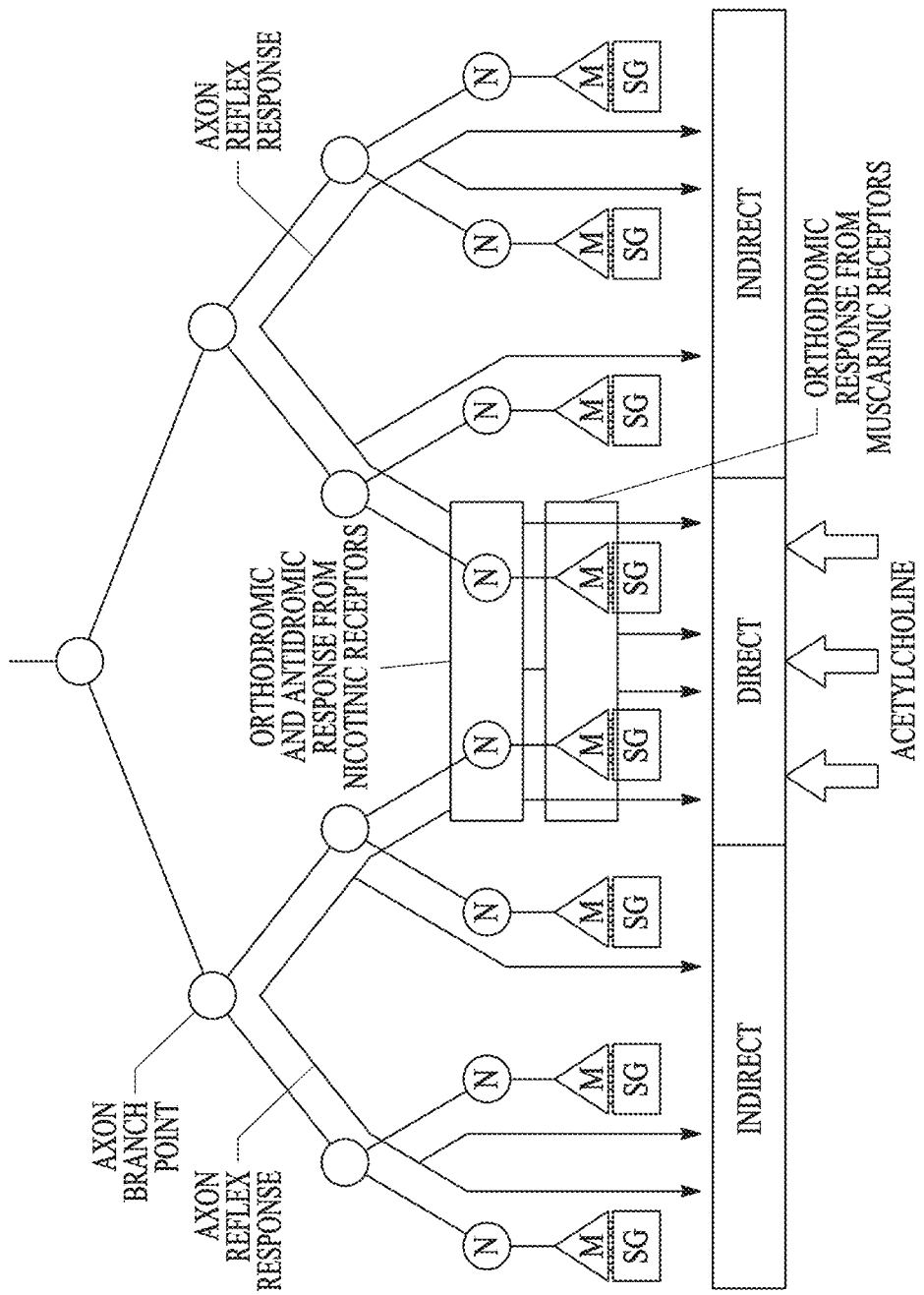
FIG. 20 illustrates a peripheral nerve network and a response to ACh.

FIGS. 19 and 20 provide simple illustrations of a peripheral nerve network that innervate sweat glands (SGs). The peripheral nerve network and sweat gland tubules include muscarinic receptors (M) and nicotinic protein receptors (N). The peripheral nerve network originates at the parent dorsal root sympathetic ganglia cells adjacent to the spinal cord, and branch off at axon branch points into distal nerve branches. These figures provide a simple illustration of only a portion of the peripheral nerve network to illustrate the direct and indirect responses.

Both pilocarpine (FIG. 19) and ACh (FIG. 20) excite proteins called muscarinic receptors that are on the sweat gland tubules. The arrows generally illustrate the iontophoresis area. The excited muscarinic receptors directly stimulate the sweat tubules to produce the direct response. Sweating from the muscarinic effect is limited to the skin directly under the area of iontophoresis.

With further reference to FIG. 20, ACh also excites nicotinic protein receptors that are present on the nerves to the SGs. The excitation wave from the nicotinic protein receptors also proceeds orthodromically toward the SGs to add to the direct stimulation of the SGs by the excited muscarinic receptors. However, the excitation wave from the nicotinic protein receptors also proceeds antidromically away from the SG, upward toward the parent dorsal root sympathetic ganglia cells adjacent to the spinal cord, causing antidromic, proximally-directed excitation toward the parent sympathetic neuron. At each axon branch encountered along the nerves the excitation also proceeds orthodromically down the distal nerve branch to activate SGs outside of the original iontophoresis area. This is referred to as an indirect response or an axon reflex response. These thin, unmyelinated sudomotor nerves that control sweating are slow-conducting nerves. Thus, the axon reflex responses are relatively slow responses, where the time for observing sweating is dependent on the length of the nerves through which the excitation travels. The inventor currently believes that the axon reflex responses are more susceptible to neuropathological influences than stimulation confined to muscarinic receptors on sweat tubules in the direct response.

FIGS. 21A-21D illustrate, by way of example, the progression of the indirect response. The iontophoresis area where the ACh was applied is on the right side of each figure. As the sudomotor nerves are thin slow conducting unmyelinated nerves, the excitation waveform takes an observable amount of time to travel from the stimulated nicotinic receptor through the various axon branches to the SGs outside of the iontophoresis area. Generally, the excitation wave travels further to reach SGs further away from the iontophoresis area than the distance it would travel to reach SGs closer to the iontophoresis area.

Figure 21A:
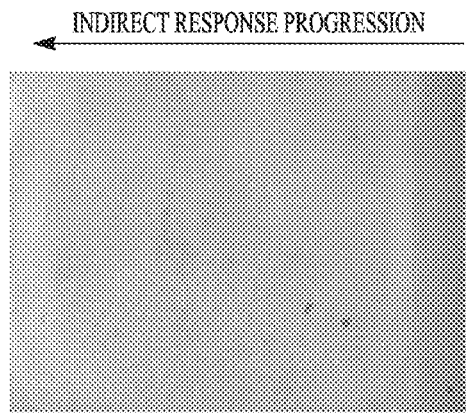
FIGS. 21A-21D illustrate a progression of an indirect response (e.g. axon reflex response) to ACh.
Figure 21B:
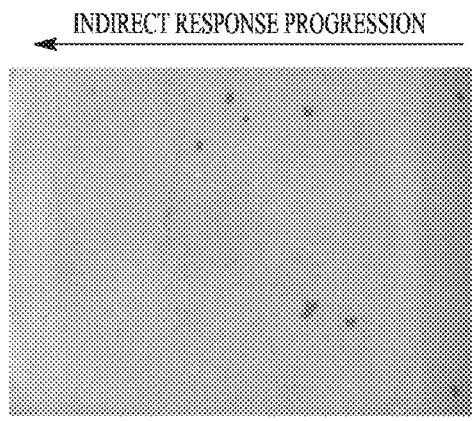
Figure 21C:
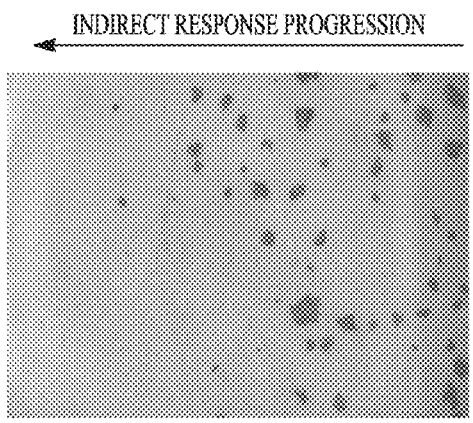
Figure 21D:
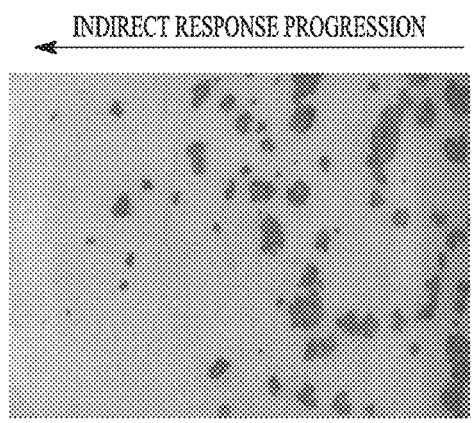

Video images of the spread of the sweat reflex away from the ACh stimulation at one edge of the field of view may be captured using a camera in close focus mode directed at a starch coated plastic strip overlying iodine-coated skin. The density of active sweat regions, sweat rates and total sweat volume may be used to assess the innervation of the test site. The dark spots on the image indicate sweat production from individual SGs in the monitored area. FIG. 21A is an image that may reflect a time within a few seconds after applying ACh. Only a few, small dark spots are observed toward the right side of the image which is relatively close to the iontophoresis area. FIGS. 21B-D illustrate a succession of images taken every few seconds (e.g. about 5 seconds) after each other. It can be seen that more-and-more SGs are excited over time, and that the wave of nerve excitation generally progresses from the right side of the image where the SGs are closer to the iontophoresis area toward the left side of the image where the SGs are further away from the iontophoresis area. A healthy network of nerves will cause the SGs to produce and cause dark spots on the image. Fewer or smaller dark spots or the absence of dark spots may indicate neuropathy. The indirect response can be monitored to detect the health of the peripheral nerve network that innervates the SGs. Furthermore, the test can be conducted several times to detect whether the peripheral nerve health is trending lower or higher. For example, the test can be performed before a drug is administered to the patient, and then performed intermittently in the days, weeks, and/or months that follow to determine at an early stage whether the drug may be having a detrimental effect on or improving the health of the peripheral nerves.

Figure 22:
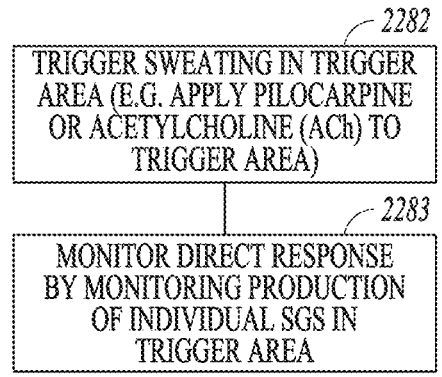
FIG. 22 provides an example of a method for monitoring the direct response.

Various embodiments monitor the direct response, the indirect response, or both the direct and indirect response to assess the health of the peripheral nerves. FIG. 22 provides an example of a method for monitoring the direct response. At 2282, sweating is triggered in a trigger area (e.g. an iontophoresis area). The direct response is monitoring the SGs in the trigger area. Either pilocarpine or ACh may be used to trigger sweating. At 2283, the direct response is monitored by monitoring production of individual SGs in the trigger area.

The following example for monitoring a direct response is provided by way of example and not limitation. Iontophoresis of either pilocarpine or ACh may be used to stimulate sweating in a small, for example ($1\times1$ cm$^2$), skin area. After iontophoresis a 1% iodine solution may be applied to the skin. Clear tape, such as packing tape, that is thinly coated with starch is stretched over the camera housing in front of the lens. The skin is wiped dry of sweat and excess iodine then immediately placing the camera housing firmly on the test site. As sweat is secreted from single sweat ducts it encounters residual iodine then starch and becomes densely blue-black. The sweat is prevented from forming droplets by the pressure of the overlying tape barrier. Instead, it is forced centrifugally in a very thin, expanding black circle. The rate that the circle expands is proportional to the sweat rate of the individual underlying SG. The expanding area of the spot is proportional to sweat volume from the same SG. The camera images the expanding black spots from 150 to 200 SGs for the $1\times1$ cm$^2$ skin area at a frame rate of 1 frame/sec for a duration of 60 seconds, or until spots from adjacent SGs begin to coalesce. Other frame rates and other frame durations may be used. Sweat rate can be calculated at any time selected during the frame duration. The response is linear. For example, the frame recorded at about 15 seconds, which is before adjacent sweat spots have coalesced may be used to calculate the sweat rate and sweat volume for the ±200

SGs, count the SGs, and scan the distribution pattern for sparse areas of presumed denervated, non-sweating glands. The majority of SGs have a low secretion rate and produce small volumes of sweat. A smaller number of SGs secrete at higher rates to produce much larger volumes. As neuropathy progresses the low volume producing glands are the first to stop sweating, presumably because of denervation. Contrary to Cannon's law completely denervated SGs do not sweat, even when exposed to the agonists pilocarpine or ACh. With progression of neuropathy, the number of innervated, active SGs declines and vacated areas appear in the distribution pattern. The effects of neuropathy can be validated histologically by immunostaining and confocal quantification of the sudomotor innervation of SGs in skin biopsies. We currently believe that the analysis of the sweat rate and volume of single SGs and counts of active SGs will be a sensitive indicator of early neuropathy and potentially an indicator of either progression of neuropathy or a measure of recovery, as expected with reinnervation. In patients receiving cancer chemotherapy such early findings can warn the physician of high susceptibility of particular patients to toxic drug effects and initiate protective changes of a drug or its dosage.

Figure 23:
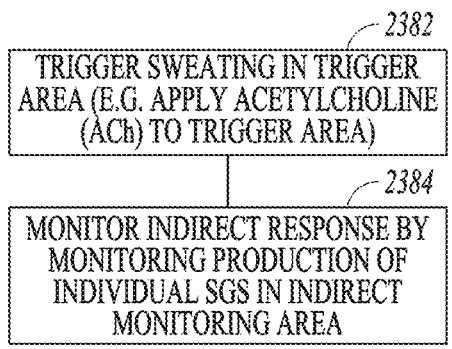
FIG. 23 provides an example of a method for monitoring the indirect response.

FIG. 23 provides an example of a method for monitoring the indirect response. At 2382, ACh is applied in a trigger area to excite the nicotinic receptors in the trigger area (e.g. iontophoresis area) to trigger an axon reflex (indirect response) that excites SGs outside of the trigger area. At 2384, the indirect response is monitored by monitoring production of individual SGs in an indirect monitoring area (e.g. an area outside of the trigger area).

It is noted that the quantitative sudomotor axons reflex test (QSART) sweat test applied ACh through iontophoresis in an annular shape (e.g. a circular trough that may be thought of as a moat, and an indirect axon reflex response occurs in the central round area which may be thought of a castle surrounded by the moat. QSART does not monitor the secretions from single SGS individually, but rather measures the amount of water secreted by these castle dwelling SGs by picking up the water with dry nitrogen or air for measurement. The volume of water from the indirect axon reflex in the castle is the reported endpoint of the QSART. Thus, as QSART does not monitor the secretions from single SGs individually, QSART does not provide a sensitive test that can provide an early indicator in the change of the health in neural networks.

It is also noted that the quantitative direct and indirect axon reflex testing (QDIRT) performed iontophoresis with ACh using 2 mA for 5 minutes in a circle of skin 10 mm in diameter. They measured sweat within the area under the iontophoresis and in an area of 20 mm diameter around the iontophoresis area. After iontophoresis they dried the skin, then sprinkled a powdered dye on the skin. As water exited the sweat pore it contacted the dye powder and became colored. It was allowed to well up and eventually the welled up drop breaks surface tension and spreads. The number of sweat spots was counted in the iontophoresis area and the area outside of the iontophoresis. Sweat droplets (spots) were measured as number, droplet (spot) size and % of the total indirect or direct areas. QDIRT is unable to provide an accurate calculation of spot volume or total volume. Instead, they correlate their total sweat spot area/time with QSART water/time. The number of spots detected was approximately 50% of the spots observed using the silicon silastic method.

The present subject matter may implement various methods to observe and record the activation of SGs by the axon reflex while it is occurring, first closer to the area of the direct response then progressively further distal. The distance depends on the length of the longest activated branch of the reflex arc. This allows comparison of direct and indirect ACh sweat responses in terms of the number, location and density of all activated SGs with the secretion rate and volume of each gland from direct and indirect stimulation.

Figure 24:
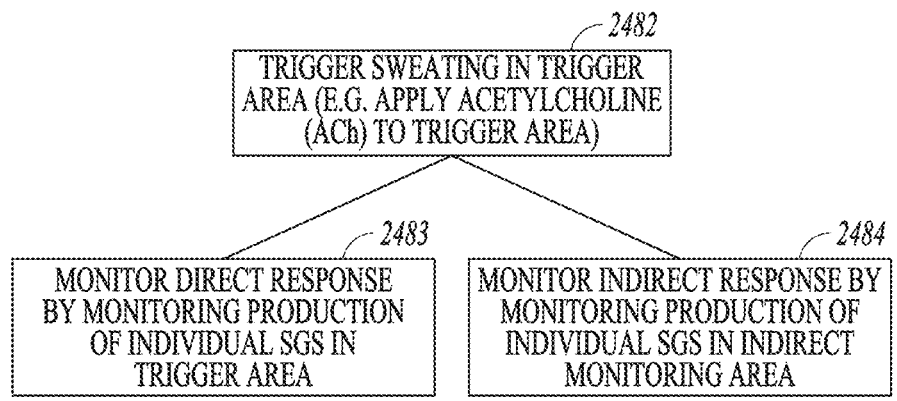
FIG. 24 provides an example of a method for monitoring both the direct and indirect response.

FIG. 24 provides an example of a method for monitoring both the direct and indirect response. At 2482, ACh is applied in a 1-2 square mm trigger area to excite both muscarinic receptors in the trigger area to trigger a direct response and nicotinic receptors in the trigger area to trigger an axon reflex (indirect response) that excites SGs outside of the trigger area. At 2483, the direct response is monitored by monitoring production of individual SGs in the trigger area. At 2484, the indirect response is monitored by monitoring production of individual SGs in an indirect monitoring area (e.g. an area outside of the trigger area where a direct response occurs).

Figure 25:
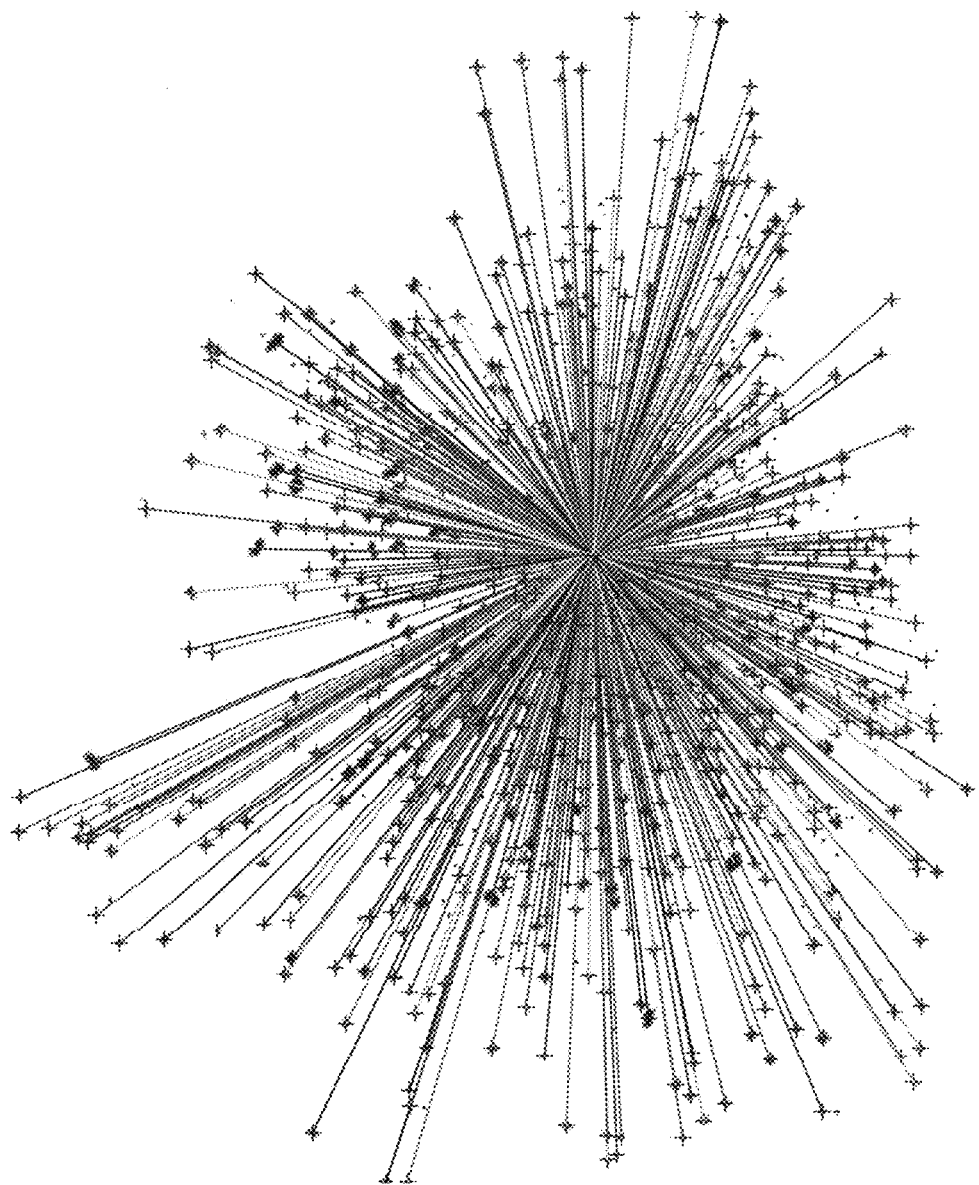
FIG. 25 illustrates, by way of example and not limitation, a graphical display of activated SGs.

A program has been develop to analyze the image(s) and to provide SG spot counts, and the distance of each spot from the center of the iontophoresis area (there are fewer spots as the distance increases). FIG. 25 illustrates, by way of example and not limitation, a graphical display of activated SGs. The display may use colored lines to assist the user in viewing the activated SGs. The lines extend from the central ACh iontophoresis area (e.g. a pinpoint). Each line extends to one activated SG (illustrated as a "+". In addition to rendering the graphical display of activated SGs, the program can be used to provide an instant count of the number of activate SGs, the size of individual activated SGs, and their distance from the central iontophoresis area. With continuous recording, sweat rate and volume may also be recorded for each individual SG and the SGs collectively. This data is more dynamic and accurate than QDIRT data. In the present subject matter, the sweat water contacts iodine (that was painted on the skin then dried) then the overlying starch covered tape that is being held flat onto the skin. The tape forces the water centrifugally in an expanding circle. This gives a better measurement of area/spot since the thickness of the secreted water layer is very small and is a controlled, constant thickness. The volume of water in the spots can be calibrated by placing similar sized drops of water on iodine stained skin (covered by starch tape to prevent evaporation) and imaged in the same manner as the experimental spots. Thus, a size of a spot on the tape is calibrated to a known quantity of water, thus providing much more precise measure of sweat spot volume. As the sweat spot is held flat by the tape, the spot is larger than QDIRT where spots are allowed to rise above the skin like an unimpeded drop of water, and the spot coalesces with adjacent spots sooner than QDIRT. The measurements are therefore not only more precise but they are made in a much shorter time. The depth of QDIRT's dark drops are not measured, and QDIRT's dark drops spread slowly and irregularly.

Figure 26:
FIG. 26 illustrates, by way of example and not limitation, an iontophoresis direct response in central area, and an indirect response as a halo or cloud around the central area.

In an example of the present subject matter, iontophoresis of ACh may be applied within a 6 mm circle to cause a 6 mm circle of directly excited SGs and a large circle (halo or cloud) of indirectly activated SGs in the surrounding skin due to the axon reflex excitation. FIG. 26 illustrates, by way of example and not limitation, an iontophoresis direct response in central area 2685, and an indirect response 2686 as a halo or cloud around the central area. The central iontophoresis direct response should normally merge almost imperceptibly with the indirect halo response. However, the pressure applied on the iontophoresis device during the iontophoresis process compromised the capillary flow, such that no sweat occurred in the circle around the direct response. The method may look at the number of spots, or the distribution and distance of the spots from the iontophoresis area. Since individual SGs are being monitored, the following information may be determined: the number of SGs in the circle, the rate of secretion of each SG, the volume each produces (and total volume to compare with QSART) if desired, the distance of each from the central circle of ACh iontophoresis, and the density of SGs at the various distances. This data may be recorded if imaged from above at a distance of about 4 inches.

Another example provides a fast method that is less precise but still provides valuable data for a fast clinical test for the office or home. The skin is painted with iodine before iontophoresis, and then the iontophoresis of ACh is applied. After stimulation, a small piece of plastic coated lightly with starch is pressed against the skin, which will indicate sweat spots, their size (for volume determinations) and distribution.

FIGS. 27A-B illustrate an example in which both a direct response and an indirect response may be monitored. In the illustrated embodiment, the trigger area 2787 (which also is the direct response area) is at the center of the region of interest, and the monitored indirect response 2788 is a region that is outside of and at least partially surrounds the trigger area. The direct response and indirect response regions may be switched, as the trigger region may be a generally annular shaped region, and the indirect response region may be in the center of the trigger region such that the trigger region generally surrounds the indirect response region. A camera 2789 positioned over both the direct response region 2787 and indirect response region 2788 can capture images that can be used to monitor individual SGs in both the direct response region and the indirect response region. As provided elsewhere in the document, a tape (not shown) can limit expansion of the depth of the sweat drops, and can also limit evaporation of the sweat. Processing software can be used to automatically detect both the areas associated with the direct and indirect response regions. The processing software can analyze production of the SGs individually or collectively for each of the direct and indirect response regions. For example, the ratio of indirect to directly activated SGs and be recorded.

FIGS. 28A-B illustrate another example in which both a direct response and an indirect response may be monitored. In the illustrated embodiment, the trigger area 2887 (which also is the direct response area) is at the left side of the image, and the indirect response region 2888 is a region that is outside of and generally to the right of the trigger area. A system may include a component 2890 to deliver the ACh through iontophoresis and a component including a camera 2889 to image the indirect monitoring area.

Figure 29A:
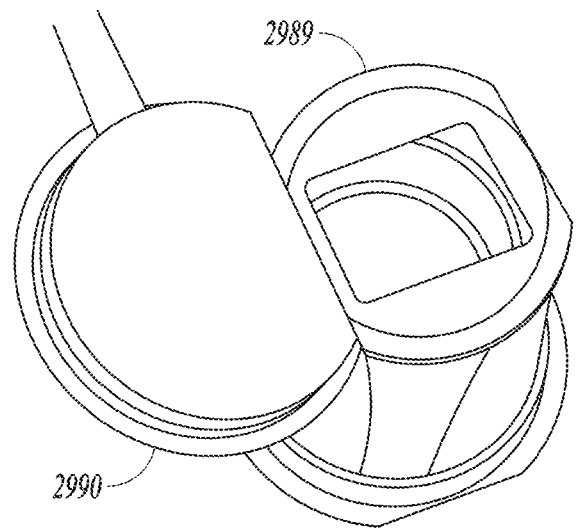
FIGS. 29A-29B illustrate an example of a system in which both a direct response and an indirect response may be monitored.
Figure 29B:
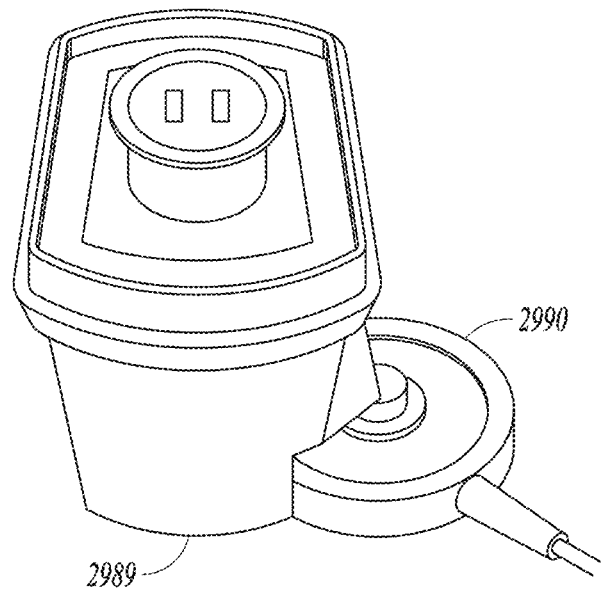

FIGS. 29A-29B illustrate an example such a system. The camera 2989 may be similar to the camera illustrated with respect to FIGS. 6A to 9. The illustrated system includes device configured to deliver iontophoresis, which may be referred to as a "side car" 2990, connected to the housing of the camera, to deliver the ACh through iontophoresis. The side car device may be a plastic device, such as may be made using 3-D printing. A gel embedded with ACh is on the side car device, such that the ACh may be delivered through iontophoresis. A user is capable of performing the test using one hand, holding the side car against the skin to deliver the ACh through iontophoresis while imaging the indirect monitoring region. The (inverted) camera has a piece of tape (not shown) with a thin cover of starch stretched over the housing that covers the lens. Iontophoresis stimulates sweating to give the underlying direct response (to be imaged later). Similar to as described above, the camera images sweat drops that are made visible by the starch iodine reaction as they are being secreted from sweat ducts onto the skin. After a few moments delay the indirect response begins to appear under the camera and is imaged. After monitoring the indirect response for about 5 minutes, the camera can be lifted and moved to image the adjacent, still active direct sweating skin. Direct and indirect sweat spot density may be compared.

Some benefits of the present subject matter include that the housing of the camera is in contact with the thin starched tape strip that is in contact with the skin. Thus, a third dimension (depth) of the sweat drop is constrained. The image rate may be between 1 to 5/sec (usually use 1/sec) for one minute until spots coalesce. This gives a precise measure of sweat rate. It has been found that the sweat rate is a straight line from the first second to 60 seconds. It has also been found that each spot has its own rate. These rates can be quite different and can decrease during neuropathy because SGs that normally received multiple nerves lose part of their innervation.

Also, the time of appearance (latency) of each sweat spot is exact. The rate of enlargement of each spot (proportional to secretion volume in nanoliters/sec.) is exact for each of 150 up to 300 hundred spots (depending upon skin site). The volume of sweat water per spot is precisely measured as the volumes have been calibrated and because there is no evaporation of sweat because of the tape cover over the spots.

One of ordinary skill in the art will understand that the modules and other circuitry shown and described herein can be implemented using software, hardware, and combinations of software and hardware. As such, the terms module and circuitry, for example, are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods are implemented using a computer data signal embodied in a carrier wave or propagated signal, that represents a sequence of instructions which, when executed by one or more processors cause the processor(s) to perform the respective method. In various embodiments, the methods are implemented as a set of instructions contained on a computer-accessible medium capable of directing a processor to perform the respective method. In various embodiments, the medium is a magnetic medium, an electronic medium, or an optical medium.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for detecting sweat production in a test area on a test subject, including:
    applying iodine on the test area and allowing the applied iodine to dry;
    triggering sweating in the test area of the test subject, including introducing acetylcholine (ACh) using iontophoresis into dermis, wherein the ACh is introduced into the dermis within an iontophoresis area;
    monitoring an indirect response to introduction of the ACh, including:
        attaching starch tape to a digital camera over an opening to the digital camera, wherein the digital camera is capable of focusing on the starch tape when the starch tape is attached over the opening to the digital camera;
        applying the starch tape, which is attached to the digital camera, over the iodine-painted test area to monitor sweat production from individual functional sweat glands (SGs) in the test area and outside of the iontophoresis area, wherein sweat production for each functional SG under a starch region of the applied starch tape results in a sweat spot on the starch tape, and wherein the starch tape is over the iodine-painted test area when the ACh is introduced into the dermis; and
        taking a series of digital images, using the digital camera, of the starch region of the starch tape when the individual, functional SGs are producing sweat and causing sweat spots on the starch tape; and
    analyzing the indirect response by analyzing the digital images of sweat spots, including analyzing individual SG sweat production produced by individual, functional SGs in the test area and outside of the iontophoresis area.

2. The method of claim 1, wherein analyzing the digital images of sweat spots includes analyzing the digital images to analyze sweat volume and sweat rate of individual, functional SGs, the method including applying a linear equation with data from a calibration of known quantities of water to convert a sweat spot area to a sweat spot volume.

3. The method of claim 1, wherein analyzing the digital images of sweat spots includes analyzing a density of sweat spots.

4. The method of claim 1, wherein analyzing the digital images of sweat spots includes analyzing the digital images to identify a location of individual, functional SGs in the iodine-painted test area outside of the iontophoresis area, and analyzing a distribution of the individual, functional SGs.

5. The method of claim 1, wherein analyzing the digital images of sweat spots includes analyzing a progression of sweat spot appearances in the series of the digital images as additional sweat spots progressively appear in a direction away from the iontophoresis area.

6. The method of claim 1, wherein analyzing the digital images of sweat spots includes tracking growth of individual, functional SGs in the test area and outside of the iontophoresis area.

7. The method of claim 1, further comprising analyzing the digital images of sweat spots includes determining a distance from each of the imaged sweat spots in the test area and outside of the iontophoresis area to a point within the iontophoresis area.

8. The method of claim 1, wherein taking the series of digital images includes taking 1-5 images per second.

9. The method of claim 1, further comprising:
    applying a device against the test subject wherein the device includes a iontophoresis component to deliver ACh through iontophoresis and includes an imaging component connected to the iontophoresis component, wherein the imaging component includes the digital camera capable of focusing on the starch tape when the starch tape is attached over the opening to the camera, the starch tape including a first side and an opposing second side, the first side having adhesive regions for attachment to the digital camera, and the second side having a starch region for placement on the test area,
    wherein the introducing ACh using iontophoresis includes using the iontophoresis component of the device that is applied against the test subject to introduce the Ach, and
    wherein the applying the device against the subject includes applying the starch tape over the iodine-painted test area when the starch tape is attached over the opening to the camera.

10. The method of claim 1, further comprising monitoring a direct response to introduction of the ACh, including applying starch tape over the iodine-painted test area to monitor individual SG sweat production from individual, functional SGs within the iontophoresis area; and
    taking a series of digital images of the starch tape when the individual, functional SGs within the iontophoresis area are producing sweat.

11. The method of claim 10, further comprising analyzing a ratio between the direct response and the indirect response.

12. The method of claim 1, wherein monitoring the indirect response includes monitoring an indirect response monitoring area that surrounds the iontophoresis area.

13. The method of claim 1, wherein monitoring the indirect response includes monitoring an indirect response monitoring area that is adjacent to and does not surround the iontophoresis area.

14. The method of claim 1, further comprising performing sweat tests, wherein performing each sweat test includes applying the iodine on the test area, triggering the sweating in the test area, monitoring the indirect response, and analyzing the digital images, the method further comprising trending results of the sweat tests to determine whether nerve health is improving or worsening.

15. The method of claim 1, wherein analyzing the digital images of sweat spots includes determining a number of sweat spots, a location for each sweat spot, a density of the sweat spots, an individual SG secretion rate for each functional SG, and an individual SG secretion volume for each functional SG.

16. A system for detecting sweat production in a test area on a test subject where dried iodine is on the test area, the test area including an iontophoresis region where acetylcholine (ACh) is to be delivered into dermis through iontophoresis and including a monitoring region, wherein the monitoring region includes an indirect monitoring region outside of the iontophoresis region, the system comprising:
    a sweat test device configured to be applied to the test area;
    the sweat test device being configured to detect sweat production of individual, functional sweat glands (SGs) within the monitoring region for analysis of individual SG sweat production produced by the individual, functional SGs, the sweat test device including;
    an iontophoresis component to deliver the ACh into the dermis through iontophoresis to the iontophoresis area and an imaging component configured to be physically connected to the iontophoresis component, the imaging component including a digital camera and a starch tape;

the sweat test device being configured to be applied to the test subject to concurrently place both the starch tape against the monitoring region area and the iontophoresis component on the iontophoresis area such that the imaging component is positioned to detect sweat production when the ACh is delivered into the dermis;

the digital camera having an opening and being configured to have the starch tape attached to the digital camera across the opening;

the digital camera being capable of focusing on the starch tape when the starch tape is placed over the opening to the digital camera; and the imaging component being configured to take a series of digital images of the starch tape while the starch tape is attached to the camera across the opening and pressed against the monitoring region including the indirect monitoring region; and a processing system configured to analyze the individual SG sweat production produced by the individual, functional SGs, provide test results for each functional SG in the monitoring region, and record the test results for each functional SG in the monitoring region.

17. The system of claim 16, wherein the processing system is configured to determine an individual SG sweat volume for each of the individual, functional SGs in the monitoring region including the indirect monitoring region, and an individual SG sweat rate for each of the individual, functional SGs in the monitoring region including the indirect monitoring region.

18. The system of claim 16, wherein the processing system is configured to track growth of sweat areas.

19. The system of claim 16, wherein the starch tape includes a first side and an opposing second side, the first side including adhesive regions for attachment to the digital camera, and the second side including a starch region for placement on the monitoring region.

* * * * *

UNITED STATES PATENT AND TRADEMARK OFFICE
CERTIFICATE OF CORRECTION

PATENT NO. : 9,918,672 B2
APPLICATION NO. : 15/153940
DATED : March 20, 2018
INVENTOR(S) : William R. Kennedy Page 1 of 1

It is certified that error appears in the above-identified patent and that said Letters Patent is hereby corrected as shown below:

On the Title Page

Item (71), in "Applicant", in Column 1, Line 1, delete "L. M." and insert --L.M.-- therefor On page 2, in Column 2, item (56), under "Other Publications", Line 24, delete ""Quantitive" and insert --"Quantitative-- therefor On page 2, in Column 2, item (56), under "Other Publications", Line 30, delete ""Regiona land" and insert --"Regional and-- therefor On page 2, in Column 2, item (56), under "Other Publications", Line 30, delete "functionof" and insert --function of-- therefor In the Claims In Column 24, Line 15, in Claim 9, delete "Ach," and insert --ACh,-- therefor Signed and Sealed this
Twelfth Day of May, 2020

Andrei Iancu
*Director of the United States Patent and Trademark Office*